(12) United States Patent
Lee et al.

(10) Patent No.: US 12,732,764 B2
(45) Date of Patent: Sep. 8, 2026

(54) ELECTRONIC DEVICE FOR TINNITUS MANAGEMENT, AND OPERATING METHOD THEREFOR

(71) Applicant: SAMSUNG ELECTRONICS CO., LTD., Suwon-si (KR)

(72) Inventors: Donghyun Lee, Suwon-si (KR); Hyeyoon Seol, Seoul (KR); Soojin Kang, Seoul (KR); Iljoon Moon, Seoul (KR); Kyoungho Bang, Suwon-si (KR); Moonsik Chung, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 63 days.

(21) Appl. No.: 18/665,955

(22) Filed: May 16, 2024

(65) Prior Publication Data

US 2024/0305941 A1 Sep. 12, 2024

Related U.S. Application Data

(63) Continuation of application No. PCT/KR2022/021156, filed on Dec. 23, 2022.

(30) Foreign Application Priority Data

Jan. 17, 2022 (KR) ........................ 10-2022-0006777
Feb. 16, 2022 (KR) ........................ 10-2022-0020161

(51) Int. Cl.

*H04R 25/00* (2006.01)
*A61B 5/00* (2006.01)
*A61B 5/12* (2006.01)
*G16H 10/20* (2018.01)
*H04R 1/10* (2026.01)
*H04R 3/04* (2006.01)

(52) U.S. Cl.

CPC ............. *H04R 25/75* (2013.01); *A61B 5/128* (2013.01); *A61B 5/742* (2013.01); *A61B 5/7475* (2013.01);

(Continued)

(58) Field of Classification Search

CPC ...... H04R 25/75; H04R 2420/07; A61B 5/12; A61B 5/128; A61B 5/486; A61F 11/00
See application file for complete search history.

(56) References Cited

U.S. PATENT DOCUMENTS

2013/0039517 A1 2/2013 Nielsen et al.
2014/0146976 A1 5/2014 Rundle (Continued)

FOREIGN PATENT DOCUMENTS

CN 113349764 A 9/2021
KR 10-2015-0083663 A 7/2015

(Continued)

OTHER PUBLICATIONS

International Search Report for PCT/KR2022/021156, mailed Apr. 19, 2023, 4 pages.

(Continued)

*Primary Examiner* — David L Ton
(74) *Attorney, Agent, or Firm* — Nixon & Vanderhye P.C.

(57) ABSTRACT

An electronic device according to various embodiments comprises: a communication circuit configured to communicate with an external electronic device; a memory in which one or more sound sources and one or more test sounds for tinnitus frequency testing are stored; and at least one processor, comprising processing circuitry, wherein the memory can store instructions that when executed by at least one processor, individually and/or collectively, cause the electronic device to: transmit a first control message to the external electronic device so that the one or more test sounds are output through the external electronic device corresponding to an ear with tinnitus identified from among the left ear and the right ear on the basis of a first input; determine a tinnitus frequency corresponding to a test sound selected from among the one or more test sounds on the basis of a second input; and transmit a second control (Continued)

message to the external electronic device so that a second sound source obtained by removing a portion corresponding to the tinnitus frequency from a first sound source from among the one or more sound sources is output through the external electronic device.

20 Claims, 9 Drawing Sheets

(52) U.S. Cl.
CPC ........... *G16H 10/20* (2018.01); *H04R 1/1041* (2013.01); *H04R 3/04* (2013.01); *H04R 2420/07* (2013.01)

(56) References Cited

U.S. PATENT DOCUMENTS

| | | | |
|---|---|---|---|
| 2015/0003650 | A1 | 1/2015 | Drexler et al. |
| 2016/0183019 | A1 | 6/2016 | Baker et al. |
| 2018/0111933 | A1 | 4/2018 | Ameriks et al. |

FOREIGN PATENT DOCUMENTS

| | | | | | |
|---|---|---|---|---|---|
| KR | 20160033706 | A | | 3/2016 | |
| KR | 20160044072 | A | | 4/2016 | |
| KR | 101636949 | B1 | | 7/2016 | |
| KR | 101754840 | B1 | | 7/2017 | |
| KR | 20190067239 | A | | 6/2019 | |
| KR | 20200027795 | A | | 3/2020 | |
| KR | 20200038041 | A | | 4/2020 | |
| KR | 10-2170186 | B1 | | 10/2020 | |
| KR | 10-2020-0140145 | A | | 12/2020 | |
| KR | 20200139045 | A | * | 12/2020 | ............. A61B 5/128 |

OTHER PUBLICATIONS

Written Opinion of the ISA for PCT/KR2022/021156, mailed Apr. 19, 2023, 4 pages.

Korean Office Action dated Jul. 27, 2026 for KR Application No. 10-2022-0020161.

* cited by examiner

ELECTRONIC DEVICE FOR TINNITUS MANAGEMENT, AND OPERATING METHOD THEREFOR

CROSS-REFERENCE TO RELATED APPLICATIONS

This application is a continuation of International Application No. PCT/KR2022/021156 designating the United States, filed on Dec. 23, 2022, in the Korean Intellectual Property Receiving Office and claiming priority to Korean Patent Application Nos. 10-2022-0006777, filed on Jan. 17, 2022 and 10-2022-0020161, filed on Feb. 16, 2022, in the Korean Intellectual Property Office, the disclosures of each of which are incorporated by reference herein in their entireties.

BACKGROUND

Field

The disclosure relates to an electronic device for tinnitus management and an operating method therefor.

Description of Related Art

Tinnitus refers to a symptom of suffering due to the hearing of continuous noise even when there is no external sound stimulation. There are various causes of tinnitus, such as stress and hearing loss. Approximately 15% of the total population in Korea experience the tinnitus, approximately 8% thereof experience tinnitus symptoms which severely interfere with sleep, and approximately 1% thereof experience tinnitus symptoms which severely interfere with daily life. As such, the tinnitus has a negative influence on an individual's life.

SUMMARY

Embodiments of the disclosure may provide an electronic device for providing a user with a sound source suitable for a tinnitus characteristic for each individual based on information obtained by means of a tinnitus test and/or tinnitus questionnaire evaluation, which are/is performed in the electronic device.

Embodiments of the disclosure may provide an electronic device for interworking with a wireless earphone to perform a tinnitus test for an ear with tinnitus symptoms and allowing the wireless earphone worn on the ear to output the sound source to provide a tinnitus management method suitable for a tinnitus characteristic for each individual.

However, problems to be addressed by the disclosure are not limited to the problem described above, and may be expanded in various manners from a range which does not deviate from the spirit and scope of the disclosure.

In accordance with an example embodiment of the disclosure, an electronic device is provided. The electronic device may include: a communication circuit configured to communicate with at least one external electronic device, a memory storing at least one sound source and at least one test sound for a tinnitus frequency test, and at least one processor, comprising processing circuitry, electrically connected with the communication circuit and the memory. The memory may store instructions which, when executed, by at least one processor, individually and/or collectively, cause the electronic device to: identify an ear with tinnitus symptoms between a left ear and a right ear based on a first input for selecting a direction of the ear with the tinnitus symptoms, transmit a first control message configured to control the at least one test sound to be output through an external electronic device corresponding to the identified ear to the external electronic device through the communication circuit, determine a frequency corresponding to a selected test sound as a tinnitus frequency based on a second input for selecting the one test sound among the at least one test sound, generate a second sound source in which a portion corresponding to the tinnitus frequency is removed from a first sound source among the at least one sound source, and transmit a second control message configured to control the second sound source to be output through the external electronic device to the external electronic device through the communication circuit.

According to an example embodiment of the disclosure, a method of operating an electronic device is provided. The method may include: identifying an ear with tinnitus symptoms between a left ear and a right ear based on a first input for selecting a direction of the ear with the tinnitus symptoms, transmitting a first control message configured to control at least one test sound to be output through an external electronic device corresponding to the identified ear to the external electronic device, determining a frequency corresponding to a selected test sound as a tinnitus frequency based on a second input for selecting the one test sound among the at least one test sound, generating a second sound source in which a portion corresponding to the tinnitus frequency is removed from a first sound source among the at least one sound source, and transmitting a second control message configured to control the second sound source to be output through the external electronic device to the external electronic device.

According to various example embodiments disclosed in the disclosure, the electronic device may provide a sound source suitable for a tinnitus characteristic for each individual to manage tinnitus in a method suitable for the user.

In addition, various effects ascertained directly or indirectly through the disclosure may be provided.

BRIEF DESCRIPTION OF THE DRAWINGS

The above and other aspects, features and advantages of certain embodiments of the present disclosure will be more apparent from the following detailed description, taken in conjunction with the accompanying drawings, in which.

DETAILED DESCRIPTION

Figure 1:
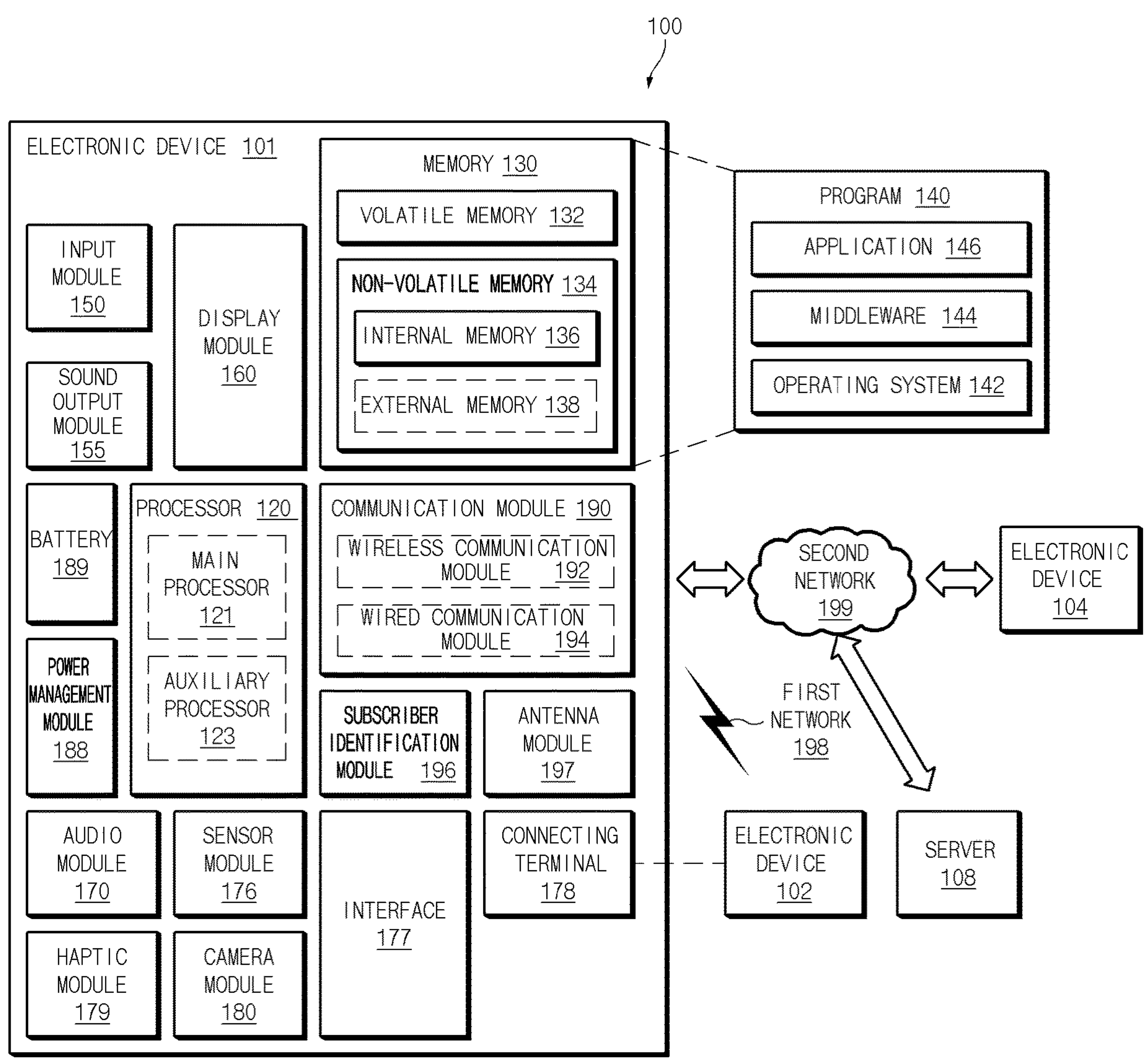
FIG. 1 is a block diagram illustrating an example electronic device in a network environment according to various embodiments.

Below, various example embodiments of the disclosure may be described with reference to accompanying drawings. Accordingly, those of ordinary skill in the art will recognize that modifications, equivalents, and/or alternatives on the various embodiments described herein may be variously made without departing from the scope and spirit of the disclosure. With regard to description of drawings, similar components may be marked by similar reference numerals.

FIG. 1 is a block diagram illustrating an example electronic device in a network environment according to various embodiments.

FIG. 1 is a block diagram illustrating an electronic device 101 in a network environment 100 according to various embodiments. Referring to FIG. 1, the electronic device 101 in the network environment 100 may communicate with an electronic device 102 via a first network 198 (e.g., a short-range wireless communication network), or at least one of an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input module 150, a sound output module 155, a display module 160, an audio module 170, a sensor module 176, an interface 177, a connecting terminal 178, a haptic module 179, a camera module 180, a power management module 188, a battery 189, a communication module 190, a subscriber identification module (SIM) 196, or an antenna module 197. In various embodiments, at least one of the components (e.g., the connecting terminal 178) may be omitted from the electronic device 101, or one or more other components may be added in the electronic device 101. In various embodiments, some of the components (e.g., the sensor module 176, the camera module 180, or the antenna module 197) may be implemented as a single component (e.g., the display module 160).

The processor 120 may include various processing circuitry and/or multiple processors. For example, as used herein, including the claims, the term “processor” may include various processing circuitry, including at least one processor, wherein one or more of at least one processor, individually and/or collectively in a distributed manner, may be configured to perform various functions described herein. As used herein, when “a processor”, “at least one processor”, and “one or more processors” are described as being configured to perform numerous functions, these terms cover situations, for example and without limitation, in which one processor performs some of recited functions and another processor(s) performs other of recited functions, and also situations in which a single processor may perform all recited functions. Additionally, the at least one processor may include a combination of processors performing various of the recited/disclosed functions, e.g., in a distributed manner. At least one processor may execute program instructions to achieve or perform various functions. The processor 120 may execute, for example, software (e.g., a program 140) to control at least one other component (e.g., a hardware or software component) of the electronic device 101 coupled with the processor 120, and may perform various data processing or computation. According to an embodiment, as at least part of the data processing or computation, the processor 120 may store a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 101 includes the main processor 121 and the auxiliary processor 123, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display module 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123. According to an embodiment, the auxiliary processor 123 (e.g., the neural processing unit) may include a hardware structure specified for artificial intelligence model processing. An artificial intelligence model may be generated by machine learning. Such learning may be performed, e.g., by the electronic device 101 where the artificial intelligence is performed or via a separate server (e.g., the server 108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input module 150 may receive a command or data to be used by another component (e.g., the processor 120) of the electronic device 101, from the outside (e.g., a user) of the electronic device 101. The input module 150 may include, for example, a microphone, a mouse, a keyboard, a key (e.g., a button), or a digital pen (e.g., a stylus pen).

The sound output module 155 may output sound signals to the outside of the electronic device 101. The sound output module 155 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display module 160 may visually provide information to the outside (e.g., a user) of the electronic device 101. The display module 160 may include, for example, a display, a hologram device, or a projector and control circuitry to control a corresponding one of the display, hologram device, and projector. According to an embodiment, the display module 160 may include a touch sensor adapted to detect a touch, or a pressure sensor adapted to measure the intensity of force incurred by the touch.

The audio module 170 may convert a sound into an electrical signal and vice versa. According to an embodiment, the audio module 170 may obtain the sound via the input module 150, or output the sound via the sound output module 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to an embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a legacy cellular network, a 5G network, a next-generation communication network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The wireless communication module 192 may support a 5G network, after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., the mmWave band) to achieve, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 192 may support various requirements specified in the electronic device 101, an external electronic device (e.g., the electronic device 104), or a network system (e.g., the second network 199). According to an embodiment, the wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device) of the electronic device 101. According to an embodiment, the antenna module 197 may include an antenna including a radiating element including a conductive material or a conductive pattern formed in or on a substrate (e.g., a printed circuit board (PCB)). According to an embodiment, the antenna module 197 may include a plurality of antennas (e.g., array antennas). In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

According to various embodiments, the antenna module 197 may form a mmWave antenna module. According to an embodiment, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 or 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra low-latency services using, e.g., distributed computing or mobile edge computing. In an embodiment, the external electronic device 104 may include an internet-of-things (IoT) device. The server 108 may be an intelligent server using machine learning and/or a neural network. According to an embodiment, the external electronic device 104 or the server 108 may be included in the second network 199. The electronic device 101 may be applied to intelligent services (e.g., smart home, smart city, smart car, or healthcare) based on 5G communication technology or IoT-related technology.

Hereinafter, a description will be given of an electronic device, a first external electronic device, and a second external electronic device according to an embodiment with reference to FIG. 2.

Figure 2:
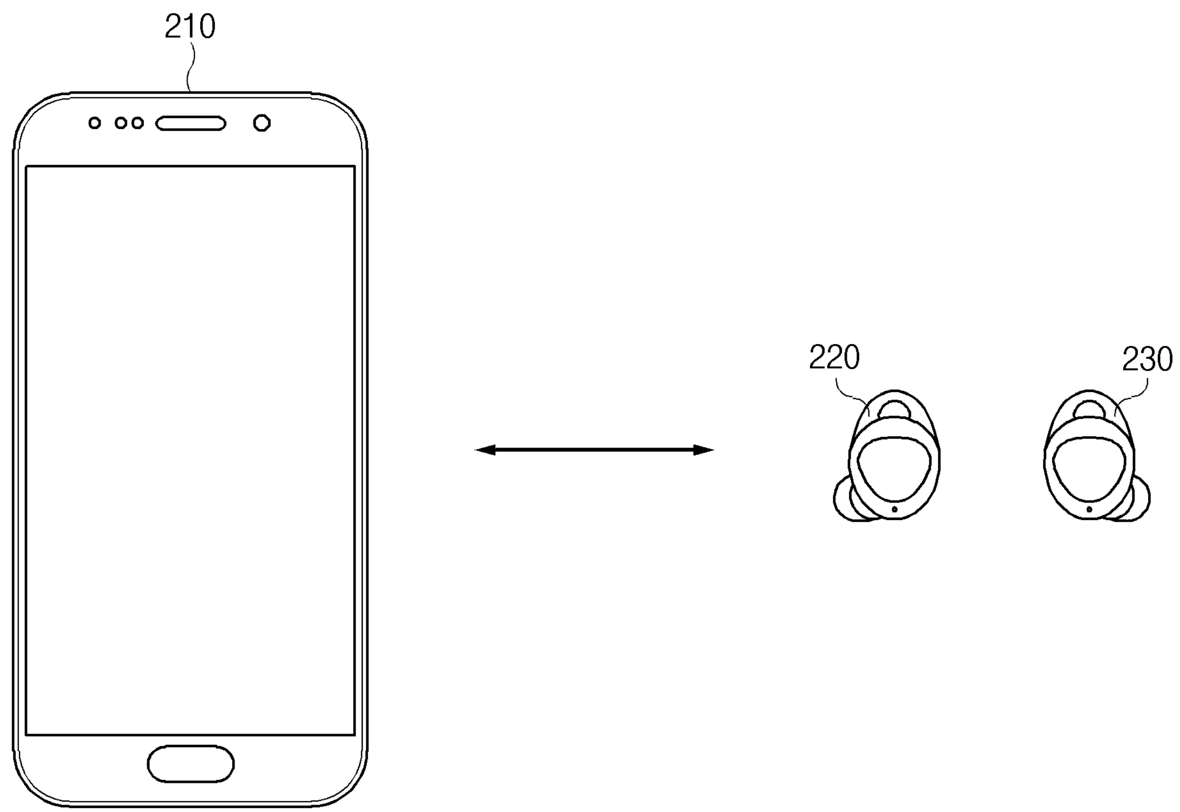
FIG. 2 is a diagram illustrating an electronic device, a first external electronic device, and a second external electronic device according to various embodiments.

FIG. 2 is a diagram illustrating an electronic device, a first external electronic device, and a second external electronic device according to various embodiments.

Referring to FIG. 2, an electronic device 210 (e.g., an electronic device 101 of FIG. 1) may transmit and receive data with a first external electronic device 220 and/or a second external electronic device 230 through a communication circuit (e.g., a wireless communication module 192 of FIG. 1). According to an embodiment, the electronic device 210 may perform wireless communication in a short range with the first external electronic device 220 and/or the second external electronic device 230 over a Bluetooth network defined by the Bluetooth special interest group (SIG). The Bluetooth network may include, for example, a Bluetooth legacy network and a Bluetooth low energy (BLE) network. According to an embodiment, the electronic device 210 may perform wireless communication with the first external electronic device 220 and/or the second external electronic device 230 over one of the Bluetooth legacy network and the BLE network or may perform wireless communication with the first external electronic device 220 and/or the second external electronic device 230 over both the Bluetooth legacy network and the BLE network.

According to an embodiment, the first external electronic device 220 and the second external electronic device 230 may be accessory devices (e.g., earphones) making up one set. For example, the first external electronic device 220 and the second external electronic device 230 may be smart earphones respectively worn on both the ears of a user. In this case, the first external electronic device 220 and the second external electronic device 230 may transmit direction information of the worn ears to the electronic device 210 through a communication circuit (e.g., a communication circuit 227 of FIG. 3). The electronic device 210 may identify which (e.g., right and left) ears of the user the first external electronic device 220 and the second external electronic device 230 are worn on, respectively, based on the received direction information of the ears.

Figure 3:
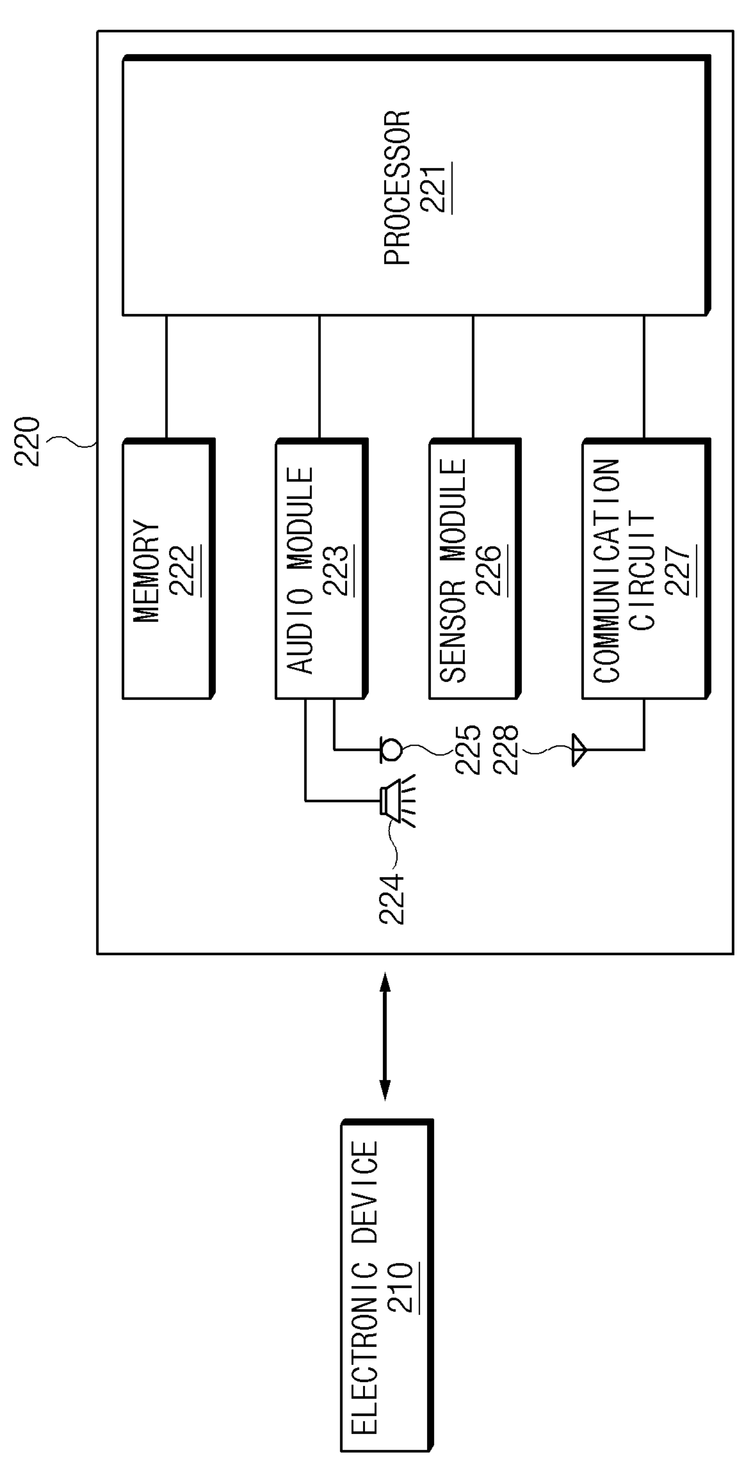
FIG. 3 is a block diagram illustrating an example configuration of a first external electronic device according to various embodiments.

The first external electronic device 220 and/or the second external electronic device 230 may receive audio data from the electronic device 210 through the communication circuit (e.g., the communication circuit 227 of FIG. 3). According to an embodiment, the first external electronic device 220 and the second external electronic device 230 may receive the same audio data from the electronic device 210. According to an embodiment, the first external electronic device 220 and the second external electronic device 230 may receive pieces of different audio data from the electronic device 210. For example, the electronic device 210 may transmit audio data which should be output to the left ear of the user to the first external electronic device 220 and may transmit audio data which should be output to the right ear of the user to the second external electronic device 230.

The first external electronic device 220 and/or the second external electronic device 230 may transmit data to the electronic device 210 through the communication circuit (e.g., the communication circuit 227 of FIG. 3).

According to an embodiment, the first external electronic device 220 and/or the second external electronic device 230 may obtain a sound wave, such as a sound or a voice, by means of a microphone (e.g., a microphone 225 of FIG. 3) and may generate an analog audio signal for it. The first external electronic device 220 and/or the second external electronic device 230 may convert the analog audio signal into audio data by means of an audio module (e.g., an audio module 223 of FIG. 3). The first external electronic device 220 and/or the second external electronic device 230 may transmit the audio data converted by the audio module to the electronic device 210.

According to an embodiment, the first external electronic device 220 and/or the second external electronic device 230 may transmit information about whether the first external electronic device 220 and/or the second external electronic device 230 are/is worn on the ear(s) of the user or biometric information of the user, which is obtained by means of a sensor module (e.g., a sensor module 226 of FIG. 3), to the electronic device 210.

Hereinafter, a description will be given of an example configuration of the first external electronic device according to an embodiment with reference to FIG. 3.

FIG. 3 is a block diagram illustrating an example configuration of a first external electronic device according to various embodiments.

Referring to FIG. 3, a first external electronic device 220 may include a processor (e.g., including processing circuitry) 221, a memory 222, an audio module (e.g., including audio circuitry) 223, a speaker 224, a microphone 225, a sensor module (e.g., including a sensor) 226, a communication circuit 227, and at least one antenna 228. According to a various embodiments, the first external electronic device 220 may not include at least one of the components of FIG. 3 or may further include one or more other components. According to various embodiments, some of the components may be implemented as one integrated circuit.

For example, the processor 221 may execute software to control at least one other component (e.g., a hardware or software component) of the first external electronic device 220, which is connected with the processor 221, and may perform a variety of data processing and calculation. According to an embodiment, as at least a portion of data processing or calculation, the processor 221 may load a command or data received from another component (e.g., the sensor module 226 or the communication circuit 227) into a volatile memory (not shown) of the memory 222, may process the command or data stored in the volatile memory, and may store the result data in a non-volatile memory (not shown). The processor 221 may include various processing circuitry and/or multiple processors. For example, as used herein, including the claims, the term "processor" may include various processing circuitry, including at least one processor, wherein one or more of at least one processor, individually and/or collectively in a distributed manner, may be configured to perform various functions described herein. As used herein, when "a processor", "at least one processor", and "one or more processors" are described as being configured to perform numerous functions, these terms cover situations, for example and without limitation, in which one processor performs some of recited functions and another processor(s) performs other of recited functions, and also situations in which a single processor may perform all recited functions. Additionally, the at least one processor may include a combination of processors performing various of the recited/disclosed functions, e.g., in a distributed manner. At least one processor may execute program instructions to achieve or perform various functions.

For example, the memory 222 may store various pieces of data used by at least one component (e.g. the processor 221 or the sensor module 226) of the first external electronic device 220. The data may include, for example, software (e.g., a program) and input data or output data for a command associated with it. The memory 222 may include the volatile memory or the nonvolatile memory. The program may be stored as software in the memory 222 and may include, for example, an operating system, middleware, or an application.

The speaker 224 may output, for example, an audio signal to the outside of the first external electronic device 220. A sound or a sound wave such as a voice may be introduced into the microphone 225 through a microphone hole. The microphone 225 may generate an electrical signal for it. The audio module 223 may convert a sound into an electrical signal, or conversely, may convert an electrical signal into a sound. The audio module 223 may obtain a sound by means of the microphone 225 or may output a sound through the speaker 224.

According to an embodiment, the audio module 223 may include various audio circuitry and support an audio data collection function. The audio module 223 may play the collected audio data. The audio module 223 may include an audio decoder, an audio encoder, a digital-to-analog (D/A) converter, or an analog-to-digital (A/D) converter. The audio decoder may convert the audio data stored in the memory 222 into a digital audio signal. The D/A converter may convert the digital audio signal converted by the audio decoder into an analog audio signal. The speaker 224 may output the analog audio signal converted by the D/A converter. The A/D converter may convert the analog audio signal obtained by means of the microphone 225 into a digital audio signal. The audio encoder may convert the digital audio signal converted by the A/D converter into audio data. The memory 222 may store the audio data converted by the audio encoder.

For example, the sensor module 226 may include at least one sensor and sense an operation state (e.g., power or a temperature) of the first electronic device 220 or an external environment state (e.g., a user state) and may generate an electrical signal corresponding to the sensed state. The electrical signal may include a data value for the sensed data. According to an embodiment, the sensor module 226 may include an acceleration sensor, a gyro sensor, a geomagnetic sensor, a magnetic sensor, an optical sensor, a proximity sensor, a temperature sensor, a gesture sensor, a grip sensor, or a biometric sensor.

For example, the first electronic device 220 may include an optical sensor located in the housing or at least a portion of one surface of the housing. When the optical sensor is located in the housing, a partial area of the housing, which faces the optical sensor, may be implemented to pass light or may include an opening.

The optical sensor may include an optical transmitter (e.g., a light emitting diode (LED)) for outputting light of at least one wavelength band or an optical receiver (e.g., a photodiode) for receiving light of one or more wavelength bands to generate an electrical signal. According to an embodiment, the optical sensor may sense whether the first external power device 220 is worn on the user.

In a state in which the first external electronic device 220 is worn on the eye of the user, light output from the optical transmitter of the optical sensor may be reflected from the skin of the user and may then be introduced into the optical receiver of the optical sensor. The optical receiver of the optical sensor may provide the processor 221 with an electrical signal based on the introduced light. The processor 221 may transmit the electrical signal, obtained from the optical sensor, to the electronic device 210 through the communication circuit 227.

The electronic device 210 may obtain various pieces of biometric information, such as a heart rate or a skin temperature, based on the electrical signal obtained from the first external electronic device 220. According to an embodiment, the processor 221 may obtain biometric information based on the electrical signal obtained from the optical sensor and may transmit the obtained biometric information to the electronic device 210 through the communication circuit 227 or may output the obtained biometric information through the speaker 224.

According to various embodiments, information or a signal about whether the first external electronic device 220 is worn on the eye of the user may be obtained by means of the sensor module 226. According to various embodiments, information or a signal about whether the first external electronic device 220 is coupled to an external device (e.g., a charging device (not shown) of the first external electronic device 220) may be obtained by means of the sensor module 226.

For example, the communication circuit 227 may establish a direct (e.g., wired) communication channel or a wireless communication channel between the first external electronic device 220 and the electronic device 210 and may support to communicate over the established communication channel. According to various embodiments, the communication circuit 227 may include one or more communication processors capable of operating independently of the processor 221 and supporting direct (e.g., wired) communication or wireless communication.

For example, the communication circuit 227 may transmit a signal or power to the electronic device 210 through the at least one antenna (or antenna radiator) 228 or may receive a signal or power from the electronic device 210 through the at least one antenna (or antenna radiator) 228.

According to an embodiment, the communication circuit 227 may include a wireless communication module including various communication circuitry (e.g., a short range wireless communication module or a global navigation satellite system (GNSS) communication module) or a wired communication module (e.g., a local area network (LAN) communication module or a power line communication module). The corresponding communication module among communication modules may communicate with the electronic device 210 over a first network (e.g., a short range communication network such as Bluetooth, Bluetooth low energy (BLE), near field communication (NFC), wireless-fidelity (Wi-Fi) Direct, or infrared data association (IrDA)) or a second network (e.g., a long range communication network such as the Internet or a computer network (e.g., a local area network (LAN) or a wide area network (WAN))).

Such several types of communication modules may be integrated into one component (e.g., a single chip) or may be implemented as a plurality of components (e.g., a plurality of chips) independent of each other. According to various embodiments, the first external electronic device 220 may include the plurality of antenna 228. The communication circuit 227 may select at least one antenna suitable for a communication scheme used in the communication network from the plurality of antennas 228. The signal or power may be transmitted or received between the communication circuit 227 and the electronic device 210 through the selected at least one antenna.

According to an embodiment, all or some of the operations executed by the first external electronic device 220 may be executed by the electronic device 210. For example, when the first external electronic device 220 should perform any function or service automatically or in response to a request from the user or any other device, it may request the electronic device 210 to perform at least a part of the function or service, instead of internally executing the function or service or additionally. Receiving the request, the electronic device 210 may execute at least a part of the requested function or service or may execute an additional function or service associated with the request and may deliver the result of the execution to the first external electronic device 220. The first external electronic device 220 may process the result as it is or additionally and may provide the processed result as at least a part of the response to the request.

According to various embodiments, the command or data received in the processor 221 may be transmitted or received between the first external electronic device 220 and the electronic device 210 through a server (a server 108 of FIG. 1) connected with the second network (e.g., the long range communication network such as the Internet or the computer network (e.g., the LAN or the WAN)).

According to an embodiment, the processor 221 may be configured to control various signal flow about audio data and collect and output information. The processor 221 may be configured to receive audio data from the electronic device 210 through the communication circuit 227 and store the received audio data in the memory 222. The processor 221 may be configured to receive non-volatile audio data (or download audio data) from the electronic device 210 and store the received non-volatile audio data in a non-volatile memory (not shown). The processor 221 may be configured to receive volatile audio data (or streaming audio data) from the electronic device 210 and store the received volatile audio data in a volatile memory (not shown).

According to an embodiment, the processor 221 may be configured to play and output the audio data (e.g., the non-volatile audio data or the volatile audio data) stored in the memory 222 through the speaker 224. For example, the audio module 223 may decode audio data to generate an audio signal capable of being output through the speaker 224 (e.g., play audio data). The generated audio signal may be output through the speaker 224.

According to various embodiments, a mode in which the first external electronic device 220 plays and outputs the volatile audio data or the non-volatile audio data stored in the memory 222 through the speaker 224 may pause when the state in which the first external electronic device 220 is not coupled to the eye of the user is identified by means of the sensor module 226. When the state in which the first external electronic device 220 is coupled to the eye of the user is identified by means of the sensor module 226, the mode may resume.

According to various embodiments, the first external electronic device 220 may provide a speech recognition function of generating a voice command from the analog audio signal received through the microphone 225. The voice command may be used for various functions about audio data.

According to various embodiments, the processor 221 may be electrically connected with a component (e.g., the memory 222, the audio module 223, the sensor module 226, and/or the communication circuit 227) included in the first external electronic device 220 and may control a component electrically connected with the processor 221.

The component (e.g., the processor 221, the memory 222, the audio module 223, the speaker 224, the microphone 225, the sensor module 226, the communication circuit 227, and/or the antenna 228) illustrated in FIG. 3 and the embodiment are described as an example of the first external electronic device 220 of FIG. 2, but this is merely for convenience of description, which may also be applied to the second external electronic device 230 of FIG. 2 in the same manner.

Hereinafter, a description will be given of an example operation of the electronic device according to an according to an embodiment with reference to FIG. 4.

Figure 4:
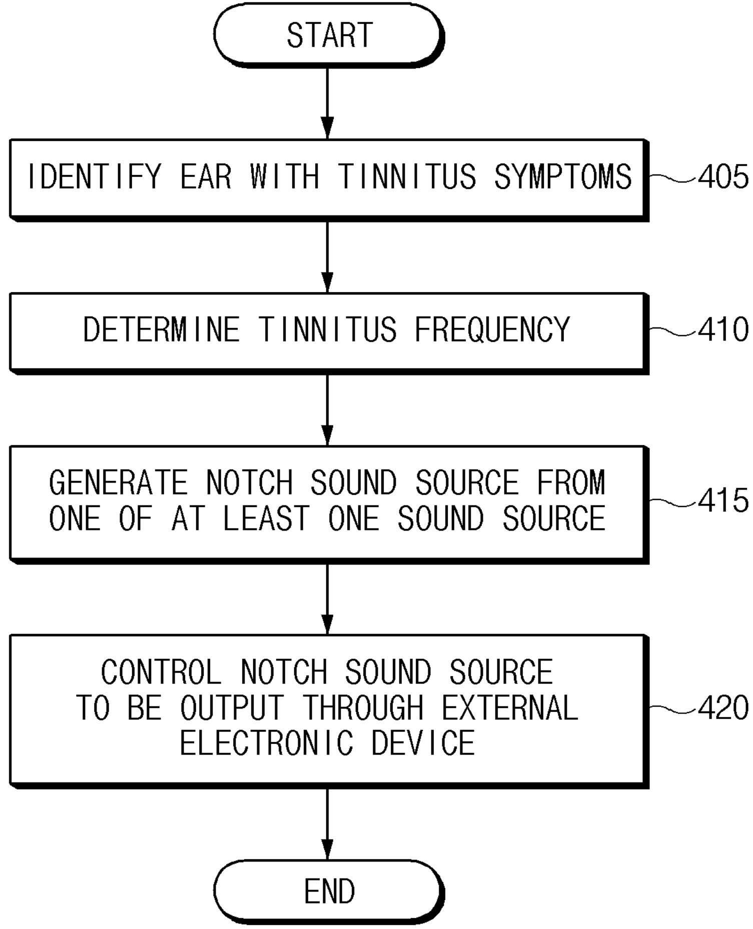
FIG. 4 is a flowchart illustrating example operations of an electronic device according to various embodiments.

FIG. 4 is a flowchart illustrating example operations of an electronic device according to various embodiments.

The embodiment illustrated in FIG. 4 is merely an example embodiment. An operation order according to various embodiments disclosed in the disclosure may be different from that illustrated in FIG. 4. Some of operations illustrated in FIG. 4 may be omitted, an order among the operations may be changed, or the operations may be merged.

According to an embodiment, operations 405 to 420 may be understood as being performed by a processor (e.g., a processor 120 of FIG. 1) of an electronic device (e.g., an electronic device 210 of FIG. 2).

Referring to FIG. 4, in operation 405, the electronic device may identify an ear with tinnitus symptoms between a left ear and a right ear of a user. The electronic device may provide a user interface to select the direction of the ear in which the user experiences the tinnitus symptoms. According to an embodiment, the electronic device may display a user interface (not shown) including a first object corresponding to the left ear and a second object corresponding to the right ear on a display (e.g., a display module 160 of FIG. 1). According to an embodiment, the electronic device may provide a user interface including a guidance voice to select the direction of the ear in which the user experiences the tinnitus symptoms. For example, the electronic device may transmit a control message for controlling the user interface including the guidance voice to be output as a voice through an external electronic device (e.g., a first external electronic device 220 of FIG. 2 and/or a second external electronic device 230 of FIG. 2) to the external electronic device through a communication circuit (e.g., a communication module 190 of FIG. 1).

According to an embodiment, the electronic device may receive a user input for selecting the direction of the ear with the tinnitus symptoms between the left ear and the right ear through the display. For example, the electronic device may display the user interface including the first object corresponding to the left ear and the second object corresponding to the right ear on the display to receive a user input for selecting the object(s) corresponding to the left ear and/or the right ear through a touch sensor (e.g., a sensor module 176 of FIG. 1) included in the display. The electronic device may identify whether the ear(s) with the tinnitus symptoms is/are the left ear or the right ear or both the ears based on the user input received through the touch sensor.

According to an embodiment, the electronic device may identify the ear with the tinnitus symptoms by means of a voice of the user. For example, the electronic device may obtain a voice of the user by means of an input module (e.g., an input module 150 of FIG. 1) and may convert the obtained voice into an electrical signal by means of an audio module (e.g., an audio module 170 of FIG. 1). The electronic device may identify whether the ear(s) with the tinnitus symptoms is/are the left ear or the right ear or both the ears based on the electrical signal converted by means of the audio module.

According to an embodiment, the electronic device may identify the ear with the tinnitus symptoms based on the audio data received from the external electronic device. For example, the electronic device may obtain a voice of the user by means of a microphone (e.g., a microphone 225 of FIG. 3) and may convert the obtained voice into audio data by means of an audio module (e.g., an audio module 223 of FIG. 3). The electronic device may receive audio data converted by means of the audio module (e.g., the audio module 223 of FIG. 3) of the external electronic device (e.g., the first external electronic device 220 and/or the second external electronic device 230 of FIG. 2) and may identify whether the ear(s) with the tinnitus symptoms is/are the left ear or the right ear or both the ears based on the received audio data.

In operation 410, the electronic device may determine a tinnitus frequency of the user. The electronic device may output at least one test sound for a tinnitus frequency test, which is stored in a memory (e.g., a memory 130 of FIG. 1), to allow the user to select a sound which is the same as or similar to his or her tinnitus sound, thus determining the tinnitus frequency.

According to an embodiment, the at least one test sound stored in the memory of the electronic device may be a sound with a specified frequency band in an audible frequency range (e.g., a range of 20 Hz to 20 KHZ). The electronic device may output the at least one test sound with the specified frequency band and may receive a user input for selecting a sound which is most similar to the tinnitus sound of the user among the output at least one of test sound. The electronic device may determine a frequency corresponding to the test sound selected based on the received user input as the tinnitus frequency. In this case, the tinnitus frequency may be determined as a frequency band (e.g., 1000 Hz to 1100 Hz) of the selected test sound.

According to an embodiment, the electronic device may classify the at least one test sound stored in the memory into a plurality of groups depending on the height of the frequency (e.g., amplitude of the frequency and/or wavelength of the frequency) and may output sounds with a center frequency band of each classified group. The electronic device may determine a first group including a sound selected based on a user input for selecting a sound which is most similar to the tinnitus sound of the user among the output sounds. According to an embodiment, the electronic device may classify at least one test sound which belongs to the first group into a plurality of groups again depending on the height of the frequency and may output sounds with a center frequency band of each classified group. The electronic device may determine a second group including the sound selected based on the user input for selecting a sound which is most similar to the tinnitus sound of the user among the output sounds. The electronic device may output at least one test sound which belongs to the second group and may receive a user input for selecting a sound which is most similar to the tinnitus sound of the user among the output at least one of test sound. The electronic device may determine a frequency corresponding to the test sound selected based on the received user input as the tinnitus frequency. To more accurately measure the tinnitus frequency of the user, the electronic device may repeat the process of classifying the at least one test sound stored in the memory into the plurality of groups depending on the height of the frequency to and determining the group including the sound which is most similar to the tinnitus sound of the user by a specified number and/or a number set by the user.

For example, the at least one test sound stored in the memory of the electronic device may include a first test sound with a bandwidth of 100 Hz (e.g., a sound with a frequency band of 20 Hz to 120 Hz) and a second test sound (e.g., a sound with a frequency band of 120 Hz to 220 Hz) to a 27th test sound (e.g., a sound with a frequency band of 2620 Hz to 2720 Hz). The user may set a process of determining a group including the signal which is most similar to his or her tinnitus sound to be repeated one time. In this case, depending on the height of the frequency, the electronic device may classify the first to 9th test sounds into a low frequency band group, may classify the 10th to 18th test sounds into a mid-frequency band group, and may classify the 19th to 27th test sounds into a high frequency band group. The electronic device may output sounds with the center frequency band of each group (e.g., the 5th test sound with a frequency band of 420 Hz to 520 Hz which is a center frequency band in a frequency band of 20 Hz to 920 Hz, for the low frequency band group). The electronic device may determine the low frequency band group including the 5th test sound selected based on a user input for selecting the 5th test sound which is most similar to the tinnitus sound of the user among the output sounds. The electronic device may output the first to 9th test sounds which belong to the low frequency band group and may receive a user input for selecting the third test sound which is most similar to the tinnitus sound of the user among the output test sounds. The electronic device may determine a frequency band of 220 Hz to 320 Hz corresponding to the third test sound as the tinnitus frequency based on the user input for selecting the third test sound.

According to an embodiment, the at least one test sound may be a pure tone with a single frequency with a frequency band of 0 in an audible frequency range (e.g., a range of 20 Hz to 20 KHZ). The electronic device may output the at least one test sound with the single frequency and may receive a user input for selecting a sound which is the same as or similar to the tinnitus sound of the user among the output at least one test sound. The electronic device may determine a single frequency corresponding to the test sound selected based on the received user input as the tinnitus frequency.

The frequency bandwidth of the at least one test sound may have various values. The frequency bandwidth (e.g., 100 Hz or 0 Hz) of the at least one test sound according to the above-mentioned embodiment is only for convenience of description, and the frequency band and/or the frequency bandwidth of the at least one test sound is not restricted or limited thereto.

According to an embodiment, the electronic device may output the at least one test sound stored in the memory through the audio module (e.g., the audio module 170 of FIG. 1) to allow the user to select the sound which is the same as or similar to his or her tinnitus sound. According to an embodiment, the electronic device may transmit a control message for controlling the at least one test sound stored in the memory to be output through the external electronic device (e.g., the first external electronic device 220 and/or the second external electronic device 230 of FIG. 2) corresponding to the ear identified as having the tinnitus symptoms in operation 405 to the external electronic device through the communication circuit (e.g., the communication module 190 of FIG. 1). In this case, the electronic device may control the at least one test sound to be output through only the external electronic device worn on the ear with the tinnitus symptoms, thus performing a more accurate tinnitus frequency test.

In operation 415, the electronic device may generate a notch sound source from one of the at least one sound source stored in the memory. According to an embodiment, the electronic device may determine a first sound source based on a user input for selecting one sound source the user wants to hear or biometric information of the user among the at least one sound source stored in the memory. According to an embodiment, the electronic device may generate the notch sound source from the determined first sound source. The notch sound source may refer to, for example, a sound source in which a portion corresponding to a specific frequency band is removed from a specific sound source. The electronic device may include a notch filter for generating the notch sound source from the first sound source. For example, the notch filter may be configured to remove the portion corresponding to the specific frequency band from the specific sound source and move the removed frequency band. The electronic device may generate the notch sound source in which the portion corresponding to the tinnitus frequency determined in operation 410 is removed from the first sound source by means of the notch filter.

According to an embodiment, when the tinnitus frequency is determined as a frequency band (e.g., 1000 Hz to 1100 Hz) in operation 410, the electronic device may generate a notch sound source in which a portion corresponding to the tinnitus frequency band (e.g., 1000 Hz to 1100 Hz) is removed from the first sound source by means of the notch filter. According to an embodiment, when the tinnitus frequency is the single frequency with the frequency band of 0 in operation 410, the electronic device may generate a notch sound source in which a portion corresponding to a frequency band which has a specified bandwidth on the basis of the tinnitus frequency is removed from the first sound source by means of the notch filter. For example, the specified bandwidth may be randomly set by the user. For example, when the tinnitus frequency is 1050 Hz and the specified bandwidth is set to 100 Hz, the electronic device may generate a notch sound source in which a portion corresponding to a frequency band of 1000 Hz to 1100 Hz is removed from the first sound source by means of the notch filter.

In operation 420, the electronic device may control the notch sound source generated in operation 415 to be output through the external electronic device. According to an embodiment, the electronic device may transmit a control message for controlling the notch sound source generated in operation 415 to be output through the external electronic device (e.g., the first external electronic device 220 of FIG. 2 and/or the second external electronic device 230 of FIG. 2) corresponding to the ear identified as having the tinnitus symptoms in operation 405 to the external electronic device through the communication circuit (e.g., the communication module 190 of FIG. 1). In this case, the electronic device may control the notch sound source to be output through only the external electronic device worn on the car with the tinnitus symptoms, thus managing tinnitus to suit a tinnitus characteristic of the user.

Hereinafter, a description will be given of an example operation of the electronic device according to an according to an embodiment with reference to FIG. 5.

Figure 5:
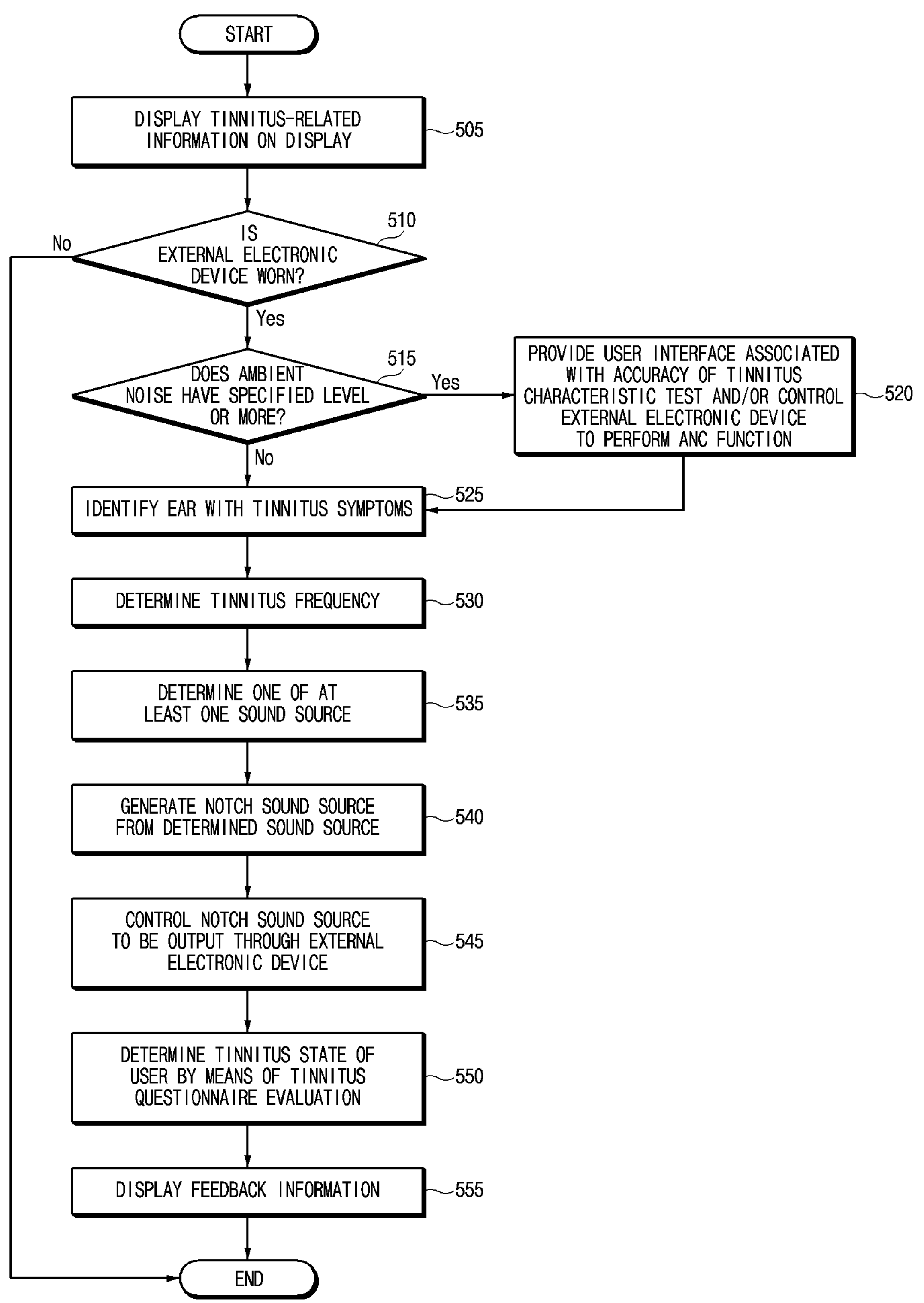
FIG. 5 is a flowchart illustrating example operations of an electronic device according to various embodiments.

FIG. 5 is a flowchart illustrating example operations of an electronic device according to various embodiments.

The embodiment illustrated in FIG. 5 is merely an example embodiment. An operation order according to various embodiments disclosed in the disclosure may be different from that illustrated in FIG. 5. Some of operations illustrated in FIG. 5 may be omitted, an order among the operations may be changed, or the operations may be merged.

According to an embodiment, operations 505 to 555 may be understood as being performed by a processor (e.g., a processor 120 of FIG. 1) of an electronic device (e.g., an electronic device 210 of FIG. 2).

Referring to FIG. 5, in operation 505, the electronic device may display tinnitus-related information on a display (e.g., a display module 160 of FIG. 1). The tinnitus-related information may include, for example, a cause of tinnitus, a tinnitus symptom alleviation method, and/or medical institution information capable of receiving tinnitus-related counseling. According to an embodiment, the electronic device may receive tinnitus-related information from an external server (e.g., an external server 710 of FIG. 7). The external server may extract and transmit tinnitus-related information capable of being helpful to a user to the electronic device based on user information (e.g., a gender, an age, or the like) and/or a tinnitus characteristic for each individual (e.g., an ear with tinnitus symptoms, a tinnitus frequency, tinnitus strength, or a duration of experiencing the tinnitus symptoms). The electronic device may display the received tinnitus-related information on the display to provide user-customized information.

In operation 510, the electronic device may determine whether an external electronic device (e.g., a first external electronic device 220 and/or a second external electronic device 230 of FIG. 2) is worn, e.g., worn on an ear of the user. According to an embodiment, the electronic device may receive information about whether the external electronic device is worn on the ear of the user, which is obtained by means of a sensor (e.g., a sensor module 226 of FIG. 3), from the external electronic device through a communication circuit (e.g., a communication module 190 of FIG. 1). The electronic device may determine whether the external electronic device is worn on the ear of the user based on the information received from the external electronic device.

When determining that the external electronic device is worn on the ear of the user in operation 510, in operation 515, the electronic device may determine whether ambient noise has a specified level or more. According to an embodiment, the electronic device may determine whether the ambient noise has the specified level or more based on ambient noise information obtained by means of an audio module (e.g., an audio module 170 of FIG. 1). According to an embodiment, the electronic device may determine whether the ambient noise has the specified level or more based on audio data received from the external electronic device through the communication circuit. The specified level may refer to, for example, a level in which the accuracy of a tinnitus characteristic test for each individual decreases to a predetermined level or more due to the ambient noise.

When determining that the ambient noise has the specified level or more in operation 515, in operation 520, the electronic device may provide a user interface associated with the accuracy of the tinnitus characteristic test and/or may control the external electronic device to perform an active noise cancellation (ANC) function.

According to an embodiment, because the tinnitus characteristic test may be inaccurate due to ambient noise, the electronic device may provide a user interface for guiding to remove the ambient noise. For example, the electronic device may display a user interface including specified guidance text on the display. The specified guidance text may include, for example, guidance text that the tinnitus characteristic test is able to be inaccurate due to ambient noise and/or guidance text to remove the ambient noise. For another example, the electronic device may transmit a control message for controlling a user interface including a specified guidance voice to be output as a voice through the external electronic device to the external electronic device through the communication circuit (e.g., the communication module 190 of FIG. 1). The specified guidance voice may include a guidance voice that the tinnitus characteristic test is able to be inaccurate due to ambient noise and/or a guidance voice to remove the ambient noise.

According to an embodiment, the electronic device may control the external electronic device to perform an ANC function for adjusting ambient noise. For example, the electronic device may transmit a control message for controlling the external electronic device to perform the ANC function for adjusting ambient noise heard by the user to have less than the specified level to the external electronic device through the communication circuit (e.g., the communication module 190 of FIG. 1).

When providing the user interface associated with the accuracy of the tinnitus characteristic test in operation 520 and/or controlling the external electronic device to perform the ANC function, in operation 525, the electronic device may identify an ear with tinnitus symptoms between a left ear and a right ear.

When determining that the ambient noise has less than the specified level in operation 515, in operation 525, the electronic device may identify the ear with the tinnitus symptoms between the left ear and the right ear of the user.

The electronic device may provide a user interface to select the direction of the ear in which the user experiences the tinnitus symptoms. According to an embodiment, the electronic device may display a user interface including a first object corresponding to the left ear and a second object corresponding to the right ear on the display. According to an embodiment, the electronic device may provide a user interface including a guidance voice to select the direction of the ear in which the user experiences the tinnitus symptoms. For example, the electronic device may transmit a control message for controlling a user interface including the guidance voice to be output as a voice through the external electronic device to the external electronic device through the communication circuit (e.g., the communication module 190 of FIG. 1).

According to an embodiment, the electronic device may receive a user input for selecting the direction of the ear with the tinnitus symptoms between the left ear and the right ear through the display. For example, the electronic device may display the user interface including the first object corresponding to the left ear and the second object corresponding to the right ear on the display to receive a user input for selecting the object(s) corresponding to the left ear and/or the right ear through a touch sensor (e.g., a sensor module 176 of FIG. 1) included in the display. The electronic device may identify whether the ear(s) with the tinnitus symptoms is the left ear or the right ear or both the ears based on the user input received through the touch sensor.

According to an embodiment, the electronic device may identify the ear with the tinnitus symptoms by means of a voice of the user. For example, the electronic device may obtain a voice of the user by means of an input module (e.g., an input module 150 of FIG. 1) and may convert the obtained voice into an electrical signal by means of the audio module (e.g., the audio module 170 of FIG. 1). The electronic device may identify whether the ear(s) with the tinnitus symptoms is/are the left ear or the right ear or both the ears based on the electrical signal converted by means of the audio module.

According to an embodiment, the electronic device may identify the ear with the tinnitus symptoms based on the audio data received from the external electronic device. For example, the external electronic device may obtain a voice of the user by means of a microphone (e.g., a microphone 225 of FIG. 3) and may convert the obtained voice into audio data by means of an audio module (e.g., an audio module 223 of FIG. 3). The electronic device may receive audio data converted by means of the audio module (e.g., the audio module 223 of FIG. 3) of the external electronic device (e.g., the first external electronic device 220 and/or the second external electronic device 230 of FIG. 2) and may identify whether the ear(s) with the tinnitus symptoms is/are the left ear or the right ear or both the ears based on the received audio data.

In operation 530, the electronic device may determine a tinnitus frequency of the user. The electronic device may output at least one test sound for a tinnitus frequency test, which is stored in a memory (e.g., a memory 130 of FIG. 1), to allow the user to select a sound which is the same as or similar to his or her tinnitus sound, thus determining the tinnitus frequency.

According to an embodiment, the at least one test sound stored in the memory of the electronic device may be a sound with a specified frequency band in an audible frequency range (e.g., a range of 20 Hz to 20 KHZ). The electronic device may output the at least one test sound with the specified frequency band and may receive a user input for selecting a sound which is most similar to the tinnitus sound of the user among the output at least one of test sound. The electronic device may determine a frequency corresponding to the test sound selected based on the received user input as the tinnitus frequency. In this case, the tinnitus frequency may be determined as a frequency band (e.g., 1000 Hz to 1100 Hz) of the selected test sound.

According to an embodiment, the electronic device may classify the at least one test sound stored in the memory into a plurality of groups depending on the height of the frequency and may output sounds with a center frequency band of each classified group. The electronic device may determine a first group including a sound selected based on a user input for selecting a sound which is most similar to the tinnitus sound of the user among the output sounds. According to an embodiment, the electronic device may classify at least one test sound which belongs to the first group into a plurality of groups again depending on the height of the frequency and may output sounds with a center frequency band of each classified group. The electronic device may determine a second group including the sound selected based on the user input for selecting a sound which is most similar to the tinnitus sound of the user among the output sounds. The electronic device may output at least one test sound which belongs to the second group and may receive a user input for selecting a sound which is most similar to the tinnitus sound of the user among the output at least one of test sound. The electronic device may determine a frequency corresponding to the test sound selected based on the received user input as the tinnitus frequency. To more accurately measure the tinnitus frequency of the user, the electronic device may repeat the process of classifying the at least one test sound stored in the memory into the plurality of groups depending on the height of the frequency and determining the group including the sound which is most similar to the tinnitus sound of the user by a specified number and/or a number set by the user.

For example, the at least one test sound stored in the memory of the electronic device may include a first test sound with a bandwidth of 100 Hz (e.g., a sound with a frequency band of 20 Hz to 120 Hz) and a second test sound (e.g., a sound with a frequency band of 120 Hz to 220 Hz) to a 27th test sound (e.g., a sound with a frequency band of 2620 Hz to 2720 Hz). The user may set a process of determining a group including the sound which is most similar to his or her tinnitus sound to be repeated one time. In this case, depending on the height of the frequency, the electronic device may classify the first to 9th test sounds into a low frequency band group, may classify the 10th to 18th test sounds into a mid-frequency band group, and may classify the 19th to 27th test sounds into a high frequency band group. The electronic device may output sounds with the center frequency band of each group (e.g., the 5th test sound with a frequency band of 420 Hz to 520 Hz which is a center frequency band in a frequency band of 20 Hz to 920 Hz, for the low frequency band group). The electronic device may determine a low frequency band group including the 5th test sound selected based on a user input for selecting the 5th test sound which is most similar to the tinnitus sound of the user among the output sounds. The electronic device may output the first to 9th test sounds which belong to the low frequency band group and may receive a user input for selecting the third test sound which is most similar to the tinnitus sound of the user among the output test sounds. The electronic device may determine a frequency band of 220 Hz to 320 Hz corresponding to the third test sound as the tinnitus frequency based on the user input for selecting the third test sound. According to an embodiment, the at least one test sound may be a pure tone with a single frequency with a frequency band of 0 in an audible frequency range (e.g., a range of 20 Hz to 20 KHZ). The electronic device may output the at least one test sound with the single frequency and may receive a user input for selecting a sound which is the same as or similar to the tinnitus sound of the user among the output at least one test sound. The electronic device may determine a single frequency corresponding to the test sound selected based on the received user input as the tinnitus frequency.

The frequency bandwidth of the at least one test sound may have various values. The frequency bandwidth (e.g., 100 Hz or 0 Hz) of the at least one test sound according to the above-mentioned embodiment is only for convenience of description, and the frequency band and/or the frequency bandwidth of the at least one test sound is not restricted or limited thereto.

According to an embodiment, the electronic device may output the at least one test sound stored in the memory through the audio module (e.g., the audio module 170 of FIG. 1) to allow the user to select a sound which is the same as or similar to his or her tinnitus sound. According to an embodiment, the electronic device may transmit a control message for controlling the at least one test sound stored in the memory to be output through the external electronic device (e.g., the first external electronic device 220 and/or the second external electronic device 230 of FIG. 2) corresponding to the ear identified as having the tinnitus symptoms in operation 525 to the external electronic device through the communication circuit (e.g., the communication module 190 of FIG. 1). In this case, the electronic device may control the at least one test sound to be output through only the external electronic device worn on the ear with the tinnitus symptoms, thus performing a more accurate tinnitus frequency test.

In operation 535, the electronic device may determine one (e.g., a sound source 615 of FIG. 6) of the at least one sound source stored in the memory. According to an embodiment, the electronic device may receive a user input for selecting one sound source the user wants to hear among the at least one sound source stored in the memory and may determine the one sound source based on the received user input. The at least one sound source may include, for example, noise, an environmental sound, music, an alarm sound, and/or a call sound.

According to an embodiment, the electronic device may receive biometric information (e.g., a heart rate or a temperature) of the user, which is detected by the external electronic device while the user hears the at least one sound source, from the external electronic device through the communication circuit. The electronic device may determine one sound source in which the stress of the user is reduced while the user is listening among the at least one sound source based on the received biometric information. The electronic device may determine one sound source in which the heart rate of the user is reduced while the user is listening among the at least one sound source.

In operation 540, the electronic device may generate a notch sound source from the sound source determined in operation 535. The notch sound source may refer to, for example, a sound source in which a portion corresponding to a specific frequency band is removed from a specific sound source. According to an embodiment, the electronic device may include a notch filter for generating a notch sound source from the sound source determined in operation 535. For example, the notch filter may be configured to remove the portion corresponding to the specific frequency band from the specific sound source and move the removed frequency band. The electronic device may generate a notch sound source in which a portion corresponding to the tinnitus frequency determined in operation 530 is removed from the sound source determined in operation 535 by means of the notch filter.

According to an embodiment, when the tinnitus frequency is determined as a frequency band (e.g., 1000 Hz to 1100 Hz) in operation 530, the electronic device may generate a notch sound source in which a portion corresponding to the tinnitus frequency band (e.g., 1000 Hz to 1100 Hz) is removed from the sound source determined in operation 535 by means of the notch filter. According to an embodiment, when the tinnitus frequency is a single frequency with a frequency band of 0 in operation 530, the electronic device may generate a notch sound source in which a portion corresponding to a frequency band which has a specified bandwidth on the basis of the tinnitus frequency is removed from the sound source determined in operation 535 by means of the notch filter. For example, the specified bandwidth may be randomly set by the user. For example, when the tinnitus frequency is 1050 Hz and the specified bandwidth is set to 100 Hz, the electronic device may generate a notch sound source in which a portion corresponding to a frequency band of 1000 Hz to 1100 Hz is removed from the sound source determined in operation 535 by means of the notch filter.

In operation 545, the electronic device may control the notch sound source generated in operation 540 to be output through the external electronic device. According to an embodiment, the electronic device may transmit a control message for controlling the notch sound source generated in operation 540 to be output through the external electronic device (e.g., the first external electronic device 220 and/or the second external electronic device 230 of FIG. 2) corresponding to the ear identified as having the tinnitus symptoms in operation 525 to the external electronic device through the communication circuit (e.g., the communication module 190 of FIG. 1). In this case, the electronic device may control the notch sound source to be output through only the external electronic device worn on the ear with the tinnitus symptoms, thus managing tinnitus to suit a tinnitus characteristic of the user.

In operation 550, the electronic device may determine a tinnitus state of the user by means of tinnitus questionnaire evaluation. According to an embodiment, the electronic device may display a user interface including a question for evaluating the tinnitus state of the user on the display. The question for evaluating the tinnitus state of the user may include, for example, a question on a tinnitus frequency of occurrence, a duration of the tinnitus, whether tinnitus symptoms are alleviated, and/or a degree to which the tinnitus symptoms are alleviated. The electronic device may determine a tinnitus state of the user based on a user input for selecting a response to the question. The tinnitus state may include, for example, a state which does not interfere with daily life, mild disability, moderate disability, and/or severe disability.

In operation 555, the electronic device may display feedback information. According to an embodiment, the electronic device may display feedback information corresponding to the tinnitus state determined in operation 550 on the display. For example, when the tinnitus state determined in operation 550 is the state which does not interferes with daily life, the electronic device may display feedback information indicates that tinnitus management is not required. For another example, when the tinnitus state determined in operation 550 is greater than or equal to the mild disability, the electronic device may display feedback information indicates that the tinnitus management is required. The feedback information may include, for example, information about whether tinnitus is alleviated, a tinnitus alleviation degree, whether tinnitus management is required, and/or a tinnitus alleviation method optimized for a tinnitus state of the user.

Hereinafter, a description will be given of an example method for generating a notch sound source in which a tinnitus frequency of the user is removed in an electronic device according to an embodiment with reference to FIG. 6.

Figure 6:
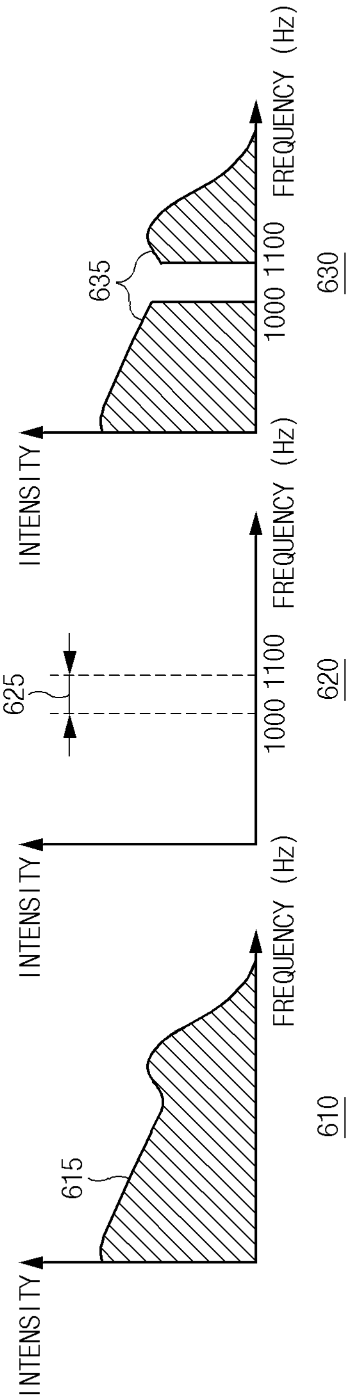
FIG. 6 is a diagram illustrating an example method for generating a notch sound source suitable for a tinnitus characteristic for each individual in an electronic device according to various embodiments.

FIG. 6 is a diagram illustrating an example method for generating a notch sound source suitable for a tinnitus characteristic for each individual in an electronic device according to various embodiments.

A sound source 615 shown in a graph 610 of FIG. 6 may be a sound source determined based on a user input in operation 535 of FIG. 5. The sound source 615 may include, for example, noise, environmental sound, music, an alarm sound, and/or a call sound.

A tinnitus frequency band 625 shown in a graph 620 of FIG. 6 may be a frequency band determined based on a user input in operation 530 of FIG. 5. According to an embodiment, when a tinnitus frequency is determined as a frequency band with a band of 1000 Hz to 1100 Hz in operation 530, the tinnitus frequency band 625 may be a frequency band with the band of 1000 Hz to 1100 Hz. According to an embodiment, when the tinnitus frequency is determined as a single frequency of 1050 Hz and a user sets a frequency bandwidth of a tinnitus sound to 100 Hz, the tinnitus frequency band 625 may be a frequency band with the band of 1000 Hz to 1100 Hz.

A notch sound source 635 shown in a graph 630 of FIG. 6 may be a notch sound source generated by means of a notch filter in operation 540 of FIG. 5. According to an embodiment, the electronic device may generate the notch sound source 635 in which a portion corresponding to the tinnitus frequency band 625 is removed from the sound source 615 by means of the notch filter.

Hereinafter, a description will be given of an electronic device, an external server, and a medical institution server according to an embodiment with reference to FIG. 7.

Figure 7:
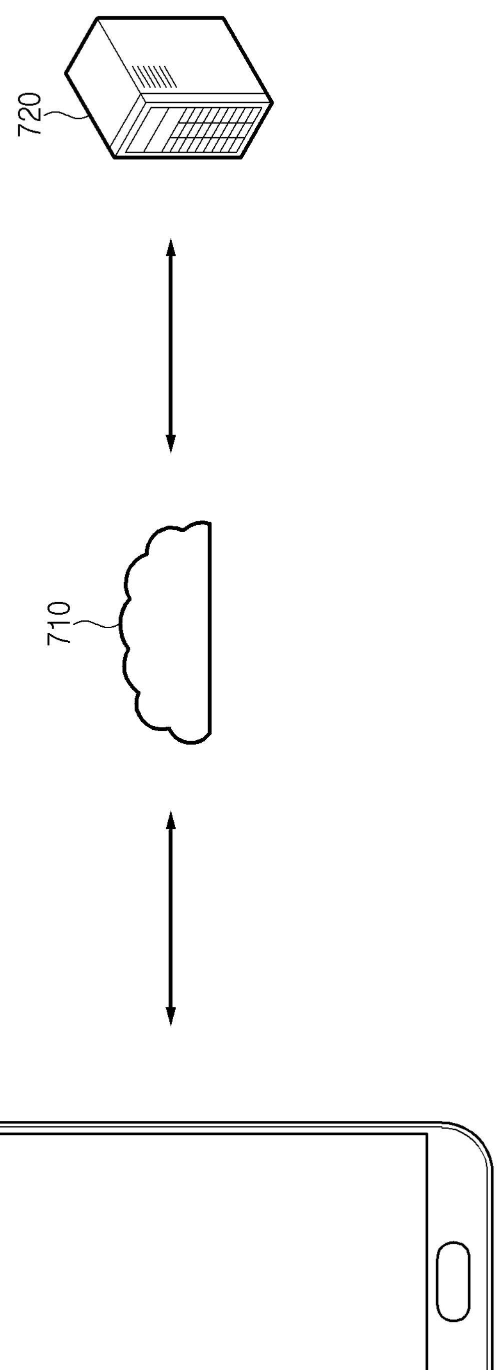
FIG. 7 is a diagram illustrating an electronic device, an external server, and a medical institution server according to various embodiments.

FIG. 7 is a diagram illustrating an electronic device, an external server, and a medical institution server according to various embodiments.

Referring to FIG. 7, a tinnitus management system according to an embodiment may include an electronic device 210 (e.g., an electronic device 101 of FIG. 1), an external server 710, and/or a medical institution server 720.

The electronic device 210 may transmit user information (e.g., information about a gender or an age) based on a user input, information about a tinnitus characteristic for each individual (e.g., information about an ear with tinnitus symptoms, a tinnitus frequency, tinnitus strength, or a duration of experiencing the tinnitus symptoms), and/or tinnitus state information for each individual based on questionnaire evaluation (e.g., information about a tinnitus alleviation degree or a preferred sound source) to the external server 710 through a communication circuit (e.g., a communication module 190 of FIG. 1).

The external server 710 may include a plurality of pieces of hardware and/or a plurality of software devices and may perform communication with the electronic device 210 and/or the medical institution server 720 over a wired or wireless communication network. According to an embodiment, the external server 710 may store information associated with a user, which is received from a plurality of electronic devices (e.g., the electronic device 210) and/or information associated with a medical institution, which is received from a plurality of medical institution servers (e.g., the medical institution server 720) to generate big data over the communication network. According to an embodiment, the external server 710 may extract a sound source for tinnitus treatment and/or feedback information, which are/is optimized for a tinnitus characteristic for each individual, based on the stored information. For example, the external server 710 may extract a sound source for tinnitus treatment and/or a tinnitus management method, which are/is most preferred in the same gender and the same age group, based on the information about the gender and age of the user. For another example, the external server 710 may extract a sound source for tinnitus treatment and/or a tinnitus management method, which have/has the highest tinnitus alleviation degree from a specific tinnitus characteristic, based on information about a tinnitus characteristic for each individual (e.g., direction information of an ear with tinnitus symptoms, tinnitus frequency information, and/or tinnitus strength information) and/or user response information about tinnitus questionnaire evaluation. The external server 710 may transmit the extracted user-customized information to the electronic device 210 over the communication network.

According to an embodiment, the external server 710 may share the stored information with the medical institution server 720 over the communication network to receive information about the user (e.g., reservation information of the user, tinnitus counseling information about the user, and/or tinnitus treatment information about the user) and/or information about a medical institution (e.g., name, location, and/or doctor information of the medical institution) from the medical institution server 720.

The medical institution server 720 may provide a customized medical service for each individual based on the information provided from the external server 710 over the communication network. According to an embodiment, the medical institution server 720 may transmit a sound source for tinnitus treatment and/or a tinnitus management method optimized for the user, which are/is generated based on user information (e.g., information about a gender and an age) provided from the external server 710 by a tinnitus-related expert, such as a doctor, information about a tinnitus characteristic for each individual (e.g., an ear with tinnitus symptoms, a tinnitus frequency, tinnitus strength, and a duration of experiencing the tinnitus symptoms), and/or tinnitus state information for each individual (e.g., information about a tinnitus alleviation degree or a preferred sound source) based on questionnaire evaluation to the external server 710 over the communication network. The external server 710 may transmit the information, received from the medical institution server 720, to the electronic device 210 to provide a customized tinnitus management method for each individual.

Hereinafter, a description will be given of an example operation of the electronic device according to an according to an embodiment with reference to FIG. 8.

Figure 8:
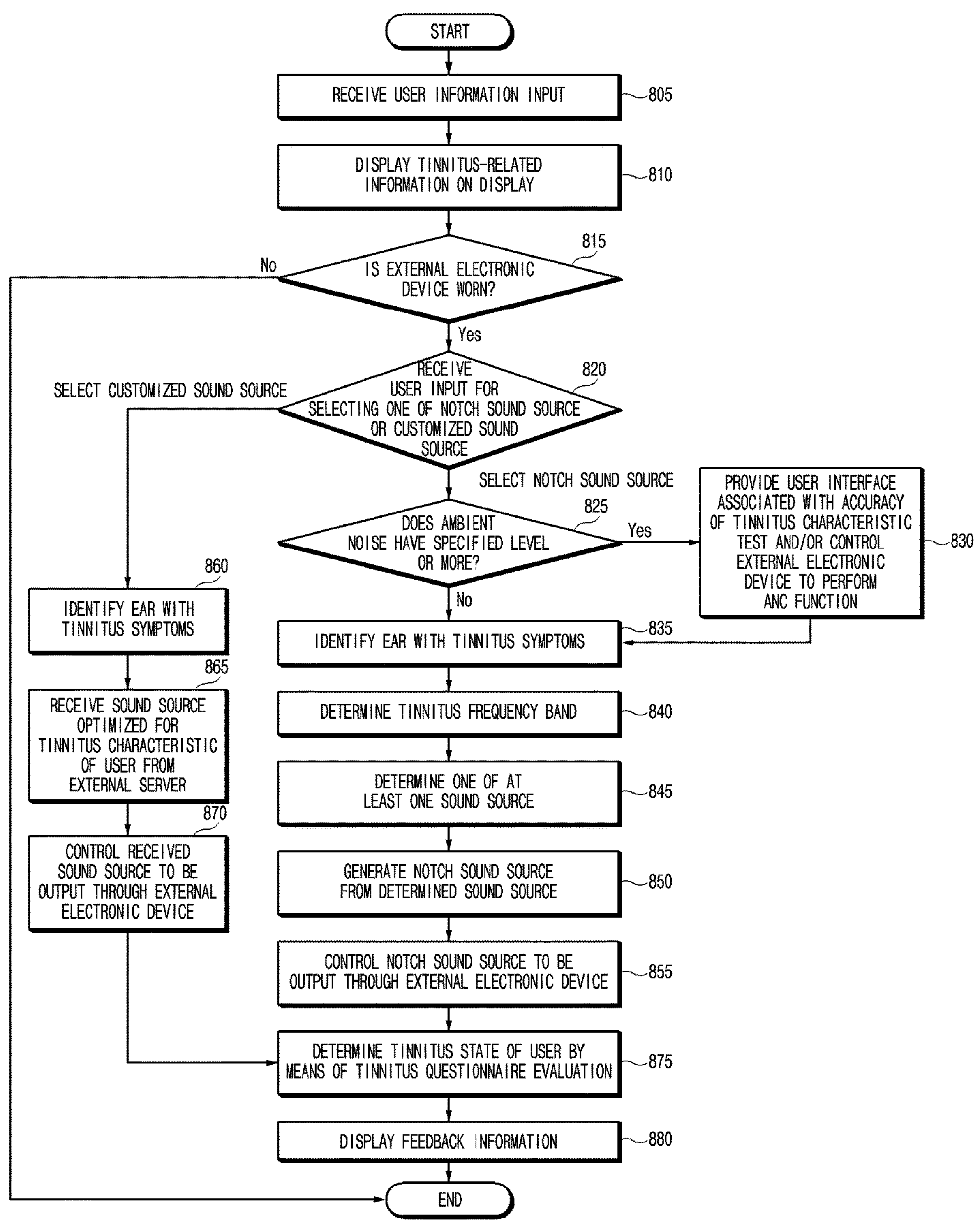
FIG. 8 is a flowchart illustrating example operations of an electronic device according to various embodiments.

FIG. 8 is a flowchart illustrating example operations of an electronic device according to various embodiments.

The embodiment illustrated in FIG. 8 is merely an example. An operation order according to various embodiments disclosed in the disclosure may be different from that illustrated in FIG. 8. Some of operations illustrated in FIG. 8 may be omitted, an order among the operations may be changed, or the operations may be merged.

According to an embodiment, operations 805 to 880 may be understood as being performed by a processor (e.g., a processor 120 of FIG. 1) of an electronic device (e.g., an electronic device 210 of FIG. 2).

Referring to FIG. 8, in operation 805, the electronic device may receive a user information input from a user. According to an embodiment, the electronic device may provide a user interface to input user information (e.g., a name, an age, and/or a gender). For example, the electronic device may display the user interface on a display (e.g., a display module 160 of FIG. 1). According to an embodiment, the electronic device may receive a user input for inputting the user information through the display. According to an embodiment, the electronic device may transmit the user information to an external server (e.g., an external server 710 of FIG. 7) through a communication circuit (e.g., a communication module 190 of FIG. 1) based on the received user input.

in operation 810, the electronic device may display tinnitus-related information on the display (e.g., the display module 160 of FIG. 1). The tinnitus-related information may include, for example, a cause of tinnitus, a tinnitus symptom alleviation method, and/or medical institution information capable of receiving tinnitus-related counseling. According to an embodiment, the electronic device may receive tinnitus-related information from the external server (e.g., the external server 710 of FIG. 7). The external server may extract and transmit tinnitus-related information capable of being helpful to the user to the electronic device based on user information (e.g., a gender, an age, or the like) and/or a tinnitus characteristic for each individual (e.g., an ear with tinnitus symptoms, a tinnitus frequency, tinnitus strength, or a duration of experiencing the tinnitus symptoms). The electronic device may display the received tinnitus-related information on the display to provide user-customized information.

In operation 815, the electronic device may determine whether an external electronic device (e.g., a first external electronic device 220 and/or a second external electronic device 230 of FIG. 2) is worn, e.g., worn on an ear of the user. According to an embodiment, the electronic device may receive information about whether the external electronic device is worn on the ear of the user, which is obtained by means of a sensor (e.g., a sensor module 226 of FIG. 3) by the external electronic device, from the external electronic device through the communication circuit (e.g., the communication module 190 of FIG. 1). The electronic device may determine whether the external electronic device is worn on the car of the user based on the information received from the external electronic device.

When determining that the external electronic device is worn on the ear of the user in operation 815, in operation 820, the electronic device may receive a user input for selecting any one of a notch sound source or a customized sound source.

According to an embodiment, the electronic device may provide a user interface to select whether to hear the notch sound source for tinnitus management or whether to hear the customized sound source. According to an embodiment, the electronic device may display a user interface including a first object corresponding to the notch sound source and a second object corresponding to the customized sound source on the display. According to an embodiment, the electronic device may provide a user interface to select whether to hear the notch sound source for tinnitus management or whether to hear the customized sound source. For example, the electronic device may transmit a control message for controlling a user interface including the guidance voice to be output as a voice through the external electronic device to the external electronic device through the communication circuit (e.g., the communication module 190 of FIG. 1).

According to an embodiment, the electronic device may receive a user input for selecting a user input for selecting a sound source to be heard by the user between the notch sound source or the customized sound source through the display. For example, the electronic device may display the user interface including the first object corresponding to the notch sound source and the second object corresponding to the customized sound source on the display to receive a user input for selecting the notch sound source or the customized sound source through a touch sensor (e.g., a sensor module 176 of FIG. 1) included in the display. The electronic device may determine whether the sound source to be heard by the user is the notch sound source or the customized sound source based on the user input received through the touch sensor.

According to an embodiment, the electronic device may receive a user input for selecting a sound source to be heard by the user between the notch sound source or the customized sound source as a voice of the user. For example, the electronic device may obtain a voice of the user by means of an input module (e.g., an input module 150 of FIG. 1) and may convert the obtained voice into an electrical signal by means of an audio module (e.g., an audio module 170 of FIG. 1). The electronic device may determine whether the sound source to be heard by the user is the notch sound source or the customized sound source based on the electrical signal converted by means of the audio module.

According to an embodiment, the electronic device may determine whether the sound source to be heard by the user is the notch sound source or the customized sound source based on the audio data received from the external electronic device. For example, the external electronic device may obtain a voice of the user by means of a microphone (e.g., a microphone 225 of FIG. 3) and may convert the obtained voice into audio data by means of an audio module (e.g., an audio module 223 of FIG. 3). The electronic device may receive the audio data converted by means of the audio module (e.g., the audio module 223 of FIG. 3) of an external electronic device (e.g., a first external electronic device 220 and/or a second external electronic device 230 of FIG. 2) and may determine whether the sound source to be heard by the user is the notch sound source or the customized sound source based on the received audio data. When receiving the user input for selecting the notch sound source in operation 820, in operation 825, the electronic device may determine whether ambient noise has a specified level or more. According to an embodiment, the electronic device may determine whether the ambient noise has the specified level or more based on ambient noise information obtained by means of the audio module (e.g., the audio module 170 of FIG. 1). According to an embodiment, the electronic device may determine whether the ambient noise has the specified level or more based on the audio data received from the external electronic device through the communication circuit. The specified level may refer to, for example, a level in which the accuracy of a tinnitus characteristic test for each individual decreases to a predetermined level or more due to the ambient noise.

When determining that the ambient noise has the specified level or more in operation 825, in operation 830, the electronic device may provide a user interface associated with the accuracy of the tinnitus characteristic test and/or may control the external electronic device to perform an active noise cancellation (ANC) function.

According to an embodiment, because the tinnitus characteristic test may be inaccurate due to the ambient noise, the electronic device may provide a user interface for guiding to remove the ambient noise. For example, the electronic device may display a user interface including specified guidance text on the display. The specified guidance text may include guidance text that the tinnitus characteristic test is able to be inaccurate due to the ambient noise and/or guidance text to remove the ambient noise. For another example, the electronic device may transmit a control message for controlling a user interface including a specified guidance voice to be output as a voice through the external electronic device to the external electronic device through the communication circuit (e.g., the communication module 190 of FIG. 1). The specified guidance voice may include, for example, a guidance voice that the tinnitus characteristic test is able to be inaccurate due to the ambient noise and/or a guidance voice to remove the ambient noise.

According to an embodiment, the electronic device may control the external electronic device to perform the ANC function for adjusting ambient noise. For example, the electronic device may transmit a control message for controlling the external electronic device to perform the ANC function for adjusting ambient noise heard by the user to be less than the specified level to the external electronic device through the communication circuit (e.g., the communication module 190 of FIG. 1).

When providing the user interface associated with the accuracy of the tinnitus characteristic test in operation 830 and/or controlling the external electronic device to perform the ANC function, in operation 835, the electronic device may identify an ear with tinnitus symptoms between a left ear and a right ear.

When determining that the ambient noise has less than the specified level in operation 825, in operation 835, the electronic device may identify the ear with the tinnitus symptoms between the left ear and the right ear of the user.

The electronic device may provide a user interface to select the direction of the ear in which the user experiences the tinnitus symptoms. According to an embodiment, the electronic device may display a user interface including a first object corresponding to the left ear and a second object corresponding to the right ear on the display. According to an embodiment, the electronic device may provide a user interface including a guidance voice to select the direction of the ear in which the user experiences the tinnitus symptoms. For example, the electronic device may transmit a control message for controlling a user interface including the guidance voice to be output as a voice through the external electronic device to the external electronic device through the communication circuit (e.g., the communication module 190 of FIG. 1).

According to an embodiment, the electronic device may receive a user input for selecting the direction of the ear with the tinnitus symptoms between the left ear and the right ear through the display. For example, the electronic device may display the user interface including the first object corresponding to the left ear and the second object corresponding to the right ear on the display to receive a user input for selecting the object(s) corresponding to the left ear and/or the right ear through the touch sensor (e.g., the sensor module 176 of FIG. 1) included in the display. The electronic device may identify whether the ear(s) with the tinnitus symptoms is/are the left ear or the right ear or both the ears based on the user input received through the touch sensor.

According to an embodiment, the electronic device may identify the ear with the tinnitus symptoms by means of a voice of the user. For example, the electronic device may obtain a voice of the user by means of an input module (e.g., an input module 150 of FIG. 1) and may convert the obtained voice into an electrical signal by means of the audio module (e.g., the audio module 170 of FIG. 1). The electronic device may identify whether the ear(s) with the tinnitus symptoms is/are the left ear or the right ear or both the ears based on the electrical signal converted by means of the audio module.

According to an embodiment, the electronic device may identify the ear with the tinnitus symptoms based on the audio data received from the external electronic device. For example, the external electronic device may obtain a voice of the user by means of the microphone (e.g., the microphone 225 of FIG. 3) and may convert the obtained voice into audio data by means of the audio module (e.g., the audio module 223 of FIG. 3). The electronic device may receive the audio data converted by means of the audio module (e.g., the audio module 223 of FIG. 3) of the external electronic device (e.g., the first external electronic device 220 and/or the second external electronic device 230 of FIG. 2) and may identify whether the ear(s) with the tinnitus symptoms is/are the left ear or the right ear or both the ears based on the received audio data.

According to an embodiment, the electronic device may transmit direction information of the ear with the tinnitus symptoms to the external server (e.g., the external server 710 of FIG. 7) through the communication circuit.

In operation 840, the electronic device may determine a tinnitus frequency of the user. The electronic device may output at least one test sound stored in a memory (e.g., a memory 130 of FIG. 1) to allow the user to select a sound which is the same as or similar to his or her tinnitus sound, thus determining the tinnitus frequency.

According to an embodiment, the at least one test sound stored in the memory of the electronic device may be a sound with a specified frequency band in an audible frequency range (e.g., a range of 20 Hz to 20 KHZ). The electronic device may output the at least one test sound with the specified frequency bandwidth and may receive a user input for selecting a sound which is most similar to the tinnitus sound of the user among the output at least one of test sound. The electronic device may determine a frequency corresponding to the test sound selected based on the received user input as the tinnitus frequency. In this case, the tinnitus frequency may be determined as a frequency band (e.g., 1000 Hz to 1100 Hz) of the selected test sound.

According to an embodiment, the electronic device may classify the at least one test sound stored in the memory into a plurality of groups depending on the height of the frequency and may output sounds with a center frequency band of each classified group. The electronic device may determine a first group including a sound selected based on a user input for selecting a sound which is most similar to the tinnitus sound of the user among the output sounds. The electronic device may classify at least one test sound which belongs to the first group into a plurality of groups again depending on the height of the frequency and may output sounds with a center frequency band of each classified group. The electronic device may determine a second group including the sound selected based on the user input for selecting a sound which is most similar to the tinnitus sound of the user among the output sounds. The electronic device may output at least one test sound which belongs to the second group and may receive a user input for selecting a sound which is most similar to the tinnitus sound of the user among the output at least one of test sound. The electronic device may determine a frequency corresponding to the test sound selected based on the received user input as the tinnitus frequency. To more accurately measure the tinnitus frequency of the user, the electronic device may repeat the process of classifying the at least one test sound stored in the memory into the plurality of groups depending on the height of the frequency and determining the group including the sound which is most similar to the tinnitus sound of the user by a specified number and/or a number set by the user.

For example, the at least one test sound stored in the memory of the electronic device may include a first test sound with a bandwidth of 100 Hz (e.g., a sound with a frequency band of 20 Hz to 120 Hz) and a second test sound (e.g., a sound with a frequency band of 120 Hz to 220 Hz) to a 27th test sound (e.g., a sound with a frequency band of 2620 Hz to 2720 Hz). The user may set a process of determining a group including the signal which is most similar to his or her tinnitus sound to be repeated one time. In this case, depending on the height of the frequency, the electronic device may classify the first to 9th test sounds into a low frequency band group, may classify the 10th to 18th test sounds into a mid-frequency band group, and may classify the 19th to 27th test sounds into a high frequency band group. The electronic device may output sounds with the center frequency band of each group (e.g., the 5th test sound with a frequency band of 420 Hz to 520 Hz which is a center frequency band in a frequency band of 20 Hz to 920 Hz, for the low frequency band group). The electronic device may determine a low frequency band group including the 5th test sound selected based on a user input for selecting the 5th test sound which is most similar to the tinnitus sound of the user among the output sounds. The electronic device may output the first to 9th test sounds which belong to the low frequency band group and may receive a user input for selecting the third test sound which is most similar to the tinnitus sound of the user among the output test sounds. The electronic device may determine a frequency band of 220 Hz to 320 Hz corresponding to the third test sound as the tinnitus frequency based on the user input for selecting the third test sound.

According to an embodiment, the at least one test sound may be a pure tone with a single frequency with a frequency band of 0 in an audible frequency range (e.g., a range of 20 Hz to 20 KHZ). The electronic device may output the at least one test sound with the single frequency and may receive a user input for selecting a sound which is the same as or similar to the tinnitus sound of the user among the output at least one test sound. The electronic device may determine a single frequency corresponding to the test sound selected based on the received user input as the tinnitus frequency.

The frequency bandwidth of the at least one test sound may have various values. The frequency bandwidth (e.g., 100 Hz or 0 Hz) of the at least one test sound according to the above-mentioned embodiment is only for convenience of description, and the frequency band and/or the frequency bandwidth of the at least one test sound is not restricted or limited thereto.

According to an embodiment, the electronic device may output the at least one test sound stored in the memory through the audio module (e.g., the audio module 170 of FIG. 1) to allow the user to select a sound which is the same as or similar to his or her tinnitus sound. According to an embodiment, the electronic device may transmit a control message for controlling the at least one test sound stored in the memory to be output through the external electronic device (e.g., the first external electronic device 220 and/or the second external electronic device 230 of FIG. 2) corresponding to the ear identified as having the tinnitus symptoms in operation 835 to the external electronic device through the communication circuit (e.g., the communication module 190 of FIG. 1). In this case, the electronic device may control the at least one test sound to be output through only the external electronic device worn on the ear with the tinnitus symptoms, thus performing a more accurate tinnitus frequency test.

According to an embodiment, the electronic device may transmit tinnitus frequency information corresponding to the determined tinnitus frequency to the external server (e.g., the external server 710 of FIG. 7) through the communication circuit.

In operation 845, the electronic device may determine one (e.g., a sound source 615 of FIG. 6) of the at least one sound source stored in the memory. According to an embodiment, the electronic device may receive a user input for selecting one sound source the user wants to hear among the at least one sound source stored in the memory and may determine the one sound source based on the received user input. The at least one sound source may include, for example, noise, environmental sound, music, a notification sound, and/or a call sound.

According to an embodiment, the electronic device may receive biometric information (e.g., a heart rate or a temperature) of the user, which is detected by the external electronic device while the user hears the at least one sound source, from the external electronic device through the communication circuit. The electronic device may determine one sound source in which the stress of the user is reduced while the user is listening among the at least one sound source based on the received biometric information. For example, the electronic device may determine one sound source in which the heart rate of the user is reduced while the user is listening among the at least one sound source.

According to an embodiment, the electronic device may transmit user preference sound source information corresponding to the determined sound source to the external server (e.g., the external server 710 of FIG. 7) through the communication circuit.

In operation 850, the electronic device may generate a notch sound source from the sound source determined in operation 845. The notch sound source may refer to, for example, a sound source in which a portion corresponding to a specific frequency band is removed from a specific sound source. According to an embodiment, the electronic device may include a notch filter for generating a notch sound source from the sound source determined in operation 845. For example, the notch filter may be configured to remove the portion corresponding to the specific frequency band from the specific sound source and move the removed frequency band. The electronic device may generate a notch sound source in which a portion corresponding to the tinnitus frequency determined in operation 840 is removed from the sound source determined in operation 845 by means of the notch filter.

According to an embodiment, when the tinnitus frequency is determined as a frequency band (e.g., 1000 Hz to 1100 Hz) in operation 840, the electronic device may generate a notch sound source in which a portion corresponding to the tinnitus frequency band (e.g., 1000 Hz to 1100 Hz) is removed from the sound source determined in operation 845 by means of the notch filter. According to an embodiment, when the tinnitus frequency is determined as a single frequency with a frequency band of 0 in operation 840, the electronic device may generate a notch sound source in which a portion corresponding to a frequency band which has a specified bandwidth on the basis of the tinnitus frequency is removed from the sound source determined in operation 845 by means of the notch filter. For example, the specified bandwidth may be randomly set by the user. For example, when the tinnitus frequency is set to 1050 Hz and the specified bandwidth is set to 100 Hz, the electronic device may generate a notch sound source in which a portion corresponding to a frequency band of 1000 Hz to 1100 Hz is removed from the sound source determined in operation 845 by means of the notch filter.

In operation 855, the electronic device may control the notch sound source generated in operation 850 to be output through the external electronic device. According to an embodiment, the electronic device may transmit a control message for controlling the notch sound source generated in operation 850 to be output through the external electronic device (e.g., the first external electronic device 220 and/or the second external electronic device 230 of FIG. 2) corresponding to the ear identified as having the tinnitus symptoms in operation 835 to the external electronic device through the communication circuit (e.g., the communication module 190 of FIG. 1). In this case, the electronic device may control the notch sound source to be output through only the external electronic device worn on the ear with the tinnitus symptoms, thus managing tinnitus to suit a tinnitus characteristic of the user.

When receiving the user input for selecting the customized sound source in operation 820, in operation 860, the electronic device may identify the ear with the tinnitus symptoms between the left ear and the right ear of the user. Operation 860 may be an operation which is substantially the same as the operation of identifying the ear with the tinnitus symptoms in operation 835.

According to an embodiment, the electronic device may transmit direction information of the ear with the tinnitus symptoms to the external server (e.g., the external server 710 of FIG. 7) through the communication circuit.

In operation 865, the electronic device may receive a sound source optimized for the tinnitus characteristic of the user from the external server (e.g., the external server 710 of FIG. 7) through the communication circuit.

According to an embodiment, the external server may extract a sound source optimized for a tinnitus characteristic for individual based on user information received from a plurality of electronic devices (e.g., an electronic device 210 of FIG. 7) over a communication network, the direction information of the ear with the tinnitus symptoms, the tinnitus frequency information, the user preference sound source information, user listening sound source information, and/or the tinnitus state information. For example, the external server may extract a most preferred sound source in the same gender and the same age group based on information about the gender and age of the user. For another example, the external server may extract a sound source with the highest tinnitus alleviation degree from the specific tinnitus characteristic based on information about a tinnitus characteristic for each individual (e.g., direction information of the ear with the tinnitus symptoms, tinnitus frequency information, and/or tinnitus strength information) and/or user response information about tinnitus questionnaire evaluation. The external server may transmit the extracted sound source to the electronic device over the communication network.

In operation 870, the electronic device may control the sound source received in operation 865 to be output through the external electronic device. According to an embodiment, the electronic device may transmit a control message for controlling the sound source received in operation 865 to be output through the external electronic device (e.g., the first external electronic device 220 and/or the second external electronic device 230 of FIG. 2) corresponding to the ear identified as having the tinnitus symptoms in operation 860 to the external electronic device through the communication circuit. In this case, the electronic device may control the notch sound source to be output through only the external electronic device worn on the ear with the tinnitus symptoms, thus managing tinnitus to suit a tinnitus characteristic of the user.

In operation 875, the electronic device may determine a tinnitus state of the user by means of tinnitus questionnaire evaluation. According to an embodiment, the electronic device may display a user interface including a question for evaluating the tinnitus state of the user on the display. The question for evaluating the tinnitus state of the user may include, for example, a question on a tinnitus frequency of occurrence, a duration of the tinnitus, whether tinnitus symptoms are alleviated, and/or a tinnitus symptom alleviation degree. The electronic device may determine a tinnitus state of the user based on a user input for selecting a response to the question. The tinnitus state may include, for example, a state which does not interfere with daily life, mild disability, moderate disability, and/or severe disability.

According to an embodiment, the electronic device may transmit tinnitus state information corresponding to the determined tinnitus state to the external server (e.g., the external server 710 of FIG. 7) through the communication circuit.

In operation 880, the electronic device may display feedback information. According to an embodiment, the electronic device may display feedback information corresponding to the tinnitus state determined in operation 875 on the display. For example, when the tinnitus state determined in operation 875 is the state which does not interferes with daily life, the electronic device may display feedback information indicates that tinnitus management is not required. For another example, when the tinnitus state determined in operation 875 is greater than or equal to the mild disability, the electronic device may display feedback information indicates that tinnitus management is required. The feedback information may include, for example, information about whether tinnitus is alleviated, a tinnitus alleviation degree, whether tinnitus management is required, and/or a tinnitus alleviation method optimized for the tinnitus state of the user.

According to an embodiment, the electronic device may receive the feedback information optimized for the user from the external server (e.g., the external server 710 of FIG. 7) through the communication circuit.

According to an embodiment, the external server may extract and transmit the feedback information optimized for the user to the electronic device based on the user information received the electronic device, the direction information of the car with the tinnitus symptoms, the tinnitus frequency information, the user preference sound source information, the user listening sound source information, and/or the tinnitus state information. For example, the external server may extract a method with a high tinnitus alleviation degree among at least one method attempted by the user for tinnitus alleviation and may transmit the extracted method to the electronic device. The electronic device may display the method received from the external server as feedback information on the display.

According to an embodiment, the external server may share the user information received the electronic device, the direction information of the ear with the tinnitus symptoms, the tinnitus frequency information, the user preference sound source information, the user listening sound source information, and/or the tinnitus state information with a medical institution server (e.g., a medical institution server 720 of FIG. 7) to receive feedback information from the medical institution server and may transmit the received feedback information to the electronic device. For example, the medical institution server may transmit tinnitus counseling information and/or tinnitus treatment information optimized for the user, which are/is generated based on the user information, the direction information of the ear with the tinnitus symptoms, the tinnitus frequency information, the user preference sound source information, the user listening sound source information, and/or the tinnitus state information, which are/is provided from the external server by a tinnitus-related expert, such as a doctor, to the external server over the communication network. The external server may transmit the information, received from the medical institution server, to the electronic device. The electronic device may display the information received from the external server as feedback information on the display.

Hereinafter, a description will be given of an example method for extracting a sound source suitable for a tinnitus characteristic for each individual in an external server according to an embodiment.

Figure 9:
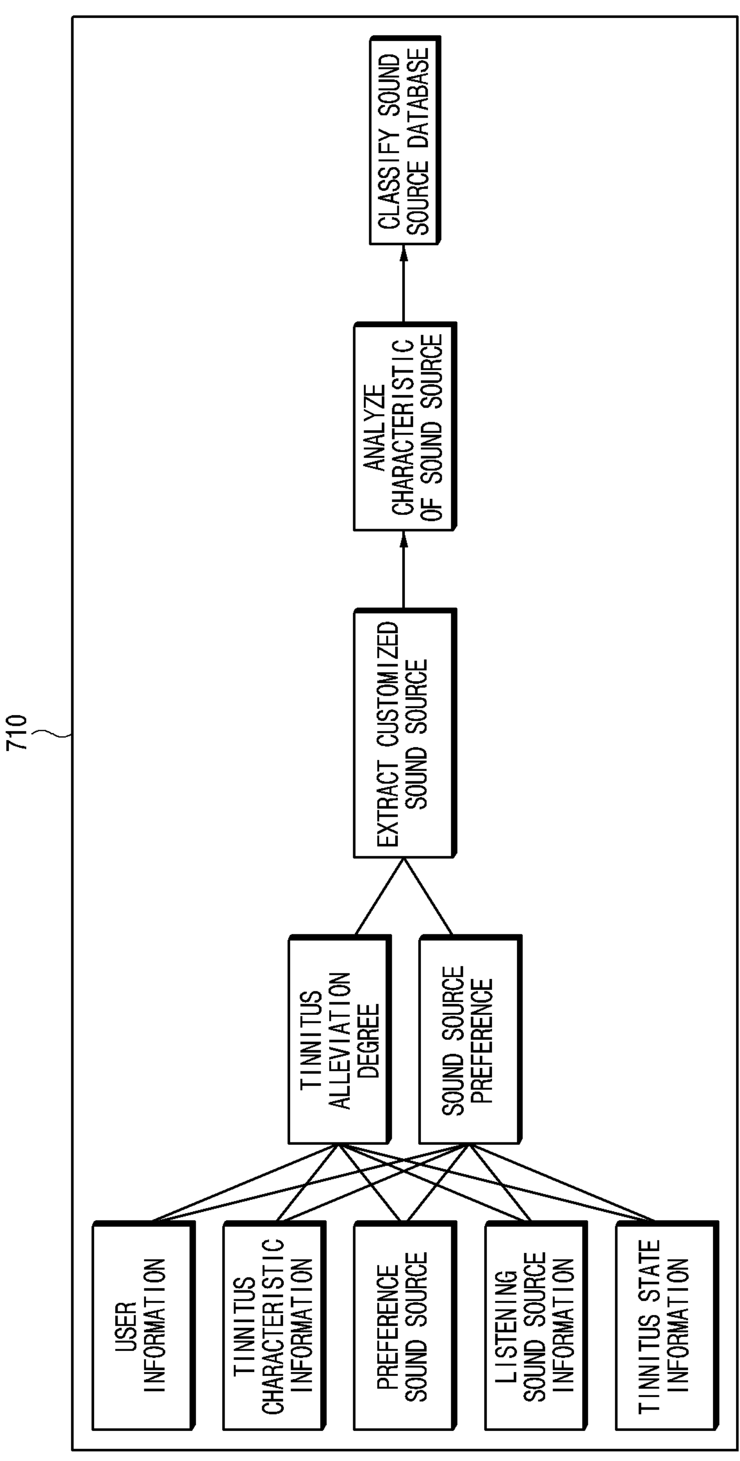
FIG. 9 is a diagram illustrating an example method for extracting a sound source suitable for a tinnitus characteristic for each individual in an external server according to various embodiments.

FIG. 9 is a diagram illustrating an example method for extracting a sound source suitable for a tinnitus characteristic for each individual in an external server according to various embodiments.

Referring to FIG. 9, an external server 710 (e.g., an external server 710 of FIG. 7) may extract a sound source suitable for a tinnitus characteristic for each individual using information received from a plurality of electronic devices (e.g., an electronic device 210 of FIG. 7) as an input parameter using, for example, a k-nearest neighbor (KNN) algorithm. Furthermore, the external server 710 may analyze characteristics of the extracted sound sources using, for example, a convolution neural network (CNN) algorithm and/or a recurrent neural network (RNN) algorithm and may store the extracted sound sources in a database depending on the characteristics of the sound sources.

According to an embodiment, the external server 710 may calculate a degree to which tinnitus symptoms are alleviated by a specific sound source heard by a user and/or a preference of the user for the specific sound source using user information received from the electronic device (e.g., the electronic device 210 of FIG. 7), tinnitus characteristic information for each individual (e.g., direction information of an ear with the tinnitus symptoms or tinnitus frequency information), user preference sound source information, listening sound source information, and/or tinnitus state information as input parameters. For example, after the user selects a first sound source in operation 845 of FIG. 8 and hears the first sound source, based on a user input for selecting a response to a question for tinnitus questionnaire evaluation performed in operation 875 of FIG. 8, the external server 710 may calculate a degree to which the tinnitus symptoms of the user are alleviated by the first sound source and/or a preference of the user for the first sound source.

According to an embodiment, the external server 710 may extract a customized sound source based on the degree to which the tinnitus symptoms are alleviated by the first sound source and/or the preference of the user for the first sound source. For example, when the degree to which the tinnitus symptoms are alleviated by the first sound source and/or the preference of the user for the first sound source are/is higher than another sound source stored in the external server 710, the external server 710 may extract the first sound source as the customized sound source.

According to an embodiment, the external server 710 may analyze a characteristic of the extracted customized sound source. For example, the external server 710 may analyze a waveform of the extracted customized sound source to analyze the characteristic of the sound source.

According to an embodiment, the external server 710 may classify, sort, and store sound sources based on the characteristic of the analyzed sound source. For example, when the extracted customized sound source is analyzed as noise, the external server 710 may classify and store the type of the customized sound source as noise.

According to an embodiment, the external server 710 may use the stored customized sound sources to extract a customized sound source of another user. For example, after another user selects a second sound source in operation 845 of FIG. 8 and hears the second sound source, based on a user input for selecting a response to a question for tinnitus questionnaire evaluation performed in operation 875 of FIG. 8, a degree to which the tinnitus symptoms of the other user are alleviated by the second sound source and/or a preference of the other user for the second sound source may be calculated. When the degree to which the tinnitus symptoms are alleviated by the second sound source and/or the preference of the other user for the second sound source are/is higher than the customized sound sources stored in the external server 710, the external server 710 may extract the second sound source as the customized sound source.

An electronic device according to an example embodiment may include: a communication circuit configured to communicate with at least one external electronic device, a memory storing at least one sound source and at least one test sound for a tinnitus frequency test, and at least one processor, comprising processing circuitry, electrically connected with the communication circuit and the memory. The memory may store instructions which, when executed, by at least one processor, individually and/or collectively, cause the electronic device to: identify an ear with tinnitus symptoms between a left ear and a right ear based on a first input selecting a direction of the ear with the tinnitus symptoms, transmit a first control message configured to control the at least one test sound to be output through an external electronic device corresponding to the identified ear to the external electronic device through the communication circuit, determine a frequency corresponding to a selected test sound as a tinnitus frequency based on a second input selecting the one test sound among the at least one test sound, generate a second sound source in which a portion corresponding to the tinnitus frequency is removed from a first sound source among the at least one sound source, and transmit a second control message configured to control the second sound source to be output through the external electronic device to the external electronic device through the communication circuit.

According to an example embodiment, the instructions, when executed by at least one processor, individually and/or collectively may cause the electronic device to: transmit first information including at least one of direction information of the ear with the tinnitus symptoms based on the first input or tinnitus frequency information based on the second input to an external server through the communication circuit, receive a third sound source optimized for a tinnitus characteristic of a user, generated based on the received first information by the external server, from the external server through the communication circuit, and transmit a third control message configured to control the third sound source to be output through the external electronic device to the external electronic device through the communication circuit.

The electronic device according to an example embodiment may further include a display. The display may be electrically connected with the processor. The instructions, when executed by at least one processor, individually and/or collectively, may cause the electronic device to: display a user interface including a question for evaluating a tinnitus state of a user on the display and determine the tinnitus state of the user based on a third input selecting a response to the question.

According to an example embodiment, the instructions, when executed by at least one processor, individually and/or collectively, may cause the electronic device to display feedback information corresponding to the determined tinnitus state on the display.

According to an example embodiment disclosed in the disclosure, the feedback information may include at least one of whether tinnitus is alleviated, a tinnitus alleviation degree, whether tinnitus management is required, or a tinnitus alleviation method optimized for the determined tinnitus state.

According to an example embodiment disclosed in the disclosure, the instructions, when executed by at least one processor, individually and/or collectively, may cause the electronic device to: transmit tinnitus state information based on the third user input to an external server through the communication circuit and receive the feedback information from the external server through the communication circuit. The feedback information may include information received from a medical institution server as the external server shares the received tinnitus state information with the medical institution server.

According to an example embodiment disclosed in the disclosure, the feedback information may include at least one of tinnitus counseling information or tinnitus treatment information.

According to an example embodiment, the instructions, when executed by at least one processor, individually and/or collectively, may cause the electronic device to: transmit second information including at least one of direction information of the ear with the tinnitus symptoms based on the first input, tinnitus frequency information based on the second input, or tinnitus state information based on the third input to an external server through the communication circuit, receive a fourth sound source optimized for a tinnitus characteristic of a user, generated based on the received second information by the external server, from the external server through the communication circuit, and transmit a fourth control message configured to control the fourth sound source to be output through the external electronic device to the external electronic device through the communication circuit.

According to an example embodiment, the instructions, when executed by at least one processor, individually and/or collectively, may cause the electronic device to receive biometric information of a user, detected by the external electronic device while the user hears the at least one sound source via the external electronic device, from the external electronic device through the communication circuit. The first sound source may include a sound source in which a heart rate of the user is reduced while hearing the at least one sound source based on the received biometric information.

The electronic device according to an example embodiment may further include a display. The display may be electrically connected with at least one processor. The instructions, when executed by at least one processor, individually and/or collectively, may cause the electronic device to display specified guidance text on the display depending on determining that ambient noise has a specified level or more based on ambient noise information. The ambient noise information may include at least one of first ambient noise information detected by the electronic device or second ambient noise information detected by the external electronic device.

A method of operating an electronic device according to an example embodiment may include: identifying an ear with tinnitus symptoms between a left ear and a right ear based on a first input selecting a direction of the ear with the tinnitus symptoms, transmitting a first control message configured to control at least one test sound to be output through an external electronic device corresponding to the identified ear to the external electronic device, determining a frequency corresponding to a selected test sound as a tinnitus frequency based on a second input selecting the one test sound among the at least one test sound, generating a second sound source in which a portion corresponding to the tinnitus frequency is removed from a first sound source among the at least one sound source, and transmitting a second control message configured to control the second sound source to be output through the external electronic device to the external electronic device.

The method of operating the electronic device according to an example embodiment may further include: transmitting first information including at least one of direction information of the ear with the tinnitus symptoms based on the first input or tinnitus frequency information based on the second input to an external server, receiving a third sound source optimized for a tinnitus characteristic of a user, generated based on the received first information by the external server, from the external server, and transmitting a third control message configured to control the third sound source to be output through the external electronic device to the external electronic device.

The method of operating the electronic device according to an example embodiment may further include: displaying a user interface including a question for evaluating a tinnitus state of a user on a display of the electronic device and determining the tinnitus state of the user based on a third input selecting a response to the question.

The method of operating the electronic device according to an example embodiment may further include displaying feedback information corresponding to the determined tinnitus state on the display.

According to an example embodiment, the feedback information may include at least one of whether tinnitus is alleviated, a tinnitus alleviation degree, whether tinnitus management is required, or a tinnitus alleviation method optimized for the determined tinnitus state.

The method of operating the electronic device according to an example embodiment may further include: transmitting tinnitus state information based on the third input to an external server and receiving the feedback information from the external server. The feedback information may include information received from a medical institution server as the external server shares the received tinnitus state information with the medical institution server.

According to an example embodiment, the feedback information may include at least one of tinnitus counseling information or tinnitus treatment information.

The method of operating the electronic device according to an example embodiment may further include: transmitting second information including at least one of direction information of the ear with the tinnitus symptoms based on the first input, tinnitus frequency information based on the second input, or tinnitus state information based on the third input to an external server, receiving a fourth sound source optimized for a tinnitus characteristic of a user, generated based on the received second information by the external server, from the external server, and transmitting a fourth control message configured to control the fourth sound source to be output through the external electronic device to the external electronic device.

The method of operating the electronic device according to an example embodiment may further include: receiving biometric information of a user, detected by the external electronic device while the user hears the at least one sound source via the external electronic device, from the external electronic device, selecting a fifth sound source in which a heart rate of the user is reduced while hearing the at least one sound source based on the received biometric information, and transmitting a fifth control message configured to control the selected fifth sound source to be output through the external electronic device to the external electronic device.

The method of operating the electronic device according to an example embodiment may further include: displaying specified guidance text on a display of the electronic device based on determining that ambient noise has a specified level or more based on ambient noise information. The ambient noise information may include at least one of first ambient noise information detected by the electronic device or second ambient noise information detected by the external electronic device.

The electronic device according to various embodiments may be one of various types of electronic devices. The electronic devices may include, for example, a portable communication device (e.g., a smartphone), a computer device, a portable multimedia device, a portable medical device, a camera, a wearable device, a home appliance, or the like. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), the element may be coupled with the other element directly (e.g., wiredly), wirelessly, or via a third element.

As used in connection with various embodiments of the disclosure, the term "module" may include a unit implemented in hardware, software, or firmware, or any combination thereof, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a compiler or a code executable by an interpreter. The machine-readable storage medium may be provided in the form of a non-transitory storage medium. Wherein, the "non-transitory" storage medium is a tangible device, and may not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities, and some of the multiple entities may be separately disposed in different components. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

While the disclosure has been illustrated and described with reference to various example embodiments, it will be understood that the various example embodiments are intended to be illustrative, not limiting. It will be further understood by those skilled in the art that various changes in form and detail may be made without departing from the true spirit and full scope of the disclosure, including the appended claims and their equivalents. It will also be understood that any of the embodiment(s) described herein may be used in conjunction with any other embodiment(s) described herein.

What is claimed is:

1. An electronic device, comprising:

a communication circuit configured to communicate with at least one external electronic device;

a memory storing at least one sound source and at least one test sound for a tinnitus frequency test; and at least one processor, comprising processing circuitry, electrically connected with the communication circuit and the memory, wherein the memory stores instructions which, when executed by at least one processor, individually and/or collectively, cause the electronic device to:

identify an ear with tinnitus symptoms between a left ear and a right ear based on a first input selecting a direction of the ear with the tinnitus symptoms;

transmit a first control message configured to control the at least one test sound to be output through an external electronic device corresponding to the identified ear to the external electronic device through the communication circuit;

determine a frequency corresponding to a selected test sound as a tinnitus frequency based on a second input selecting the one test sound among the at least one test sound output through the external electronic device;

generate a second sound source in which a portion corresponding to the tinnitus frequency is removed from a first sound source among the at least one sound source;

transmit a second control message configured to control the second sound source to be output through the external electronic device to the external electronic device through the communication circuit; and based on determining that ambient noise has a specified level or more based on ambient noise information, control the external electronic device to remove at least part of the ambient noise during output of the at least one test sound through the external electronic device.

2. The electronic device of claim 1, wherein the instructions, when executed by at least one processor, individually and/or collectively, cause the electronic device to:

transmit first information including at least one of direction information of the ear with the tinnitus symptoms based on the first input or tinnitus frequency information based on the second input to an external server through the communication circuit;

receive a third sound source optimized for a tinnitus characteristic of a user, the third sound source being generated based on the received first information by the external server, from the external server through the communication circuit; and transmit a third control message configured to control the third sound source to be output through the external electronic device to the external electronic device through the communication circuit.

3. The electronic device of claim 1, further comprising:

a display, wherein the display is electrically connected with at least one processor, and wherein the instructions, when executed by at least one processor, individually and/or collectively, cause the electronic device to:

display a user interface including a question for evaluating a tinnitus state of a user on the display; and determine the tinnitus state of the user based on a third input selecting a response to the question.

4. The electronic device of claim 3, wherein the instructions, when executed by at least one processor, individually and/or collectively, cause the electronic device to:

display feedback information corresponding to the determined tinnitus state on the display.

5. The electronic device of claim 4, wherein the feedback information includes at least one of whether tinnitus is alleviated, a tinnitus alleviation degree, whether tinnitus management is required, or a tinnitus alleviation method optimized for the determined tinnitus state.

6. The electronic device of claim 4, wherein the instructions, when executed by at least one processor, individually and/or collectively, cause the electronic device to:

transmit tinnitus state information based on the third input to an external server through the communication circuit; and receive the feedback information from the external server through the communication circuit, and wherein the feedback information includes information received from a medical institution server as the external server shares the received tinnitus state information with the medical institution server.

7. The electronic device of claim 6, wherein the feedback information includes at least one of tinnitus counseling information or tinnitus treatment information.

8. The electronic device of claim 3, wherein the instructions, when executed by at least one processor, individually and/or collectively, cause the electronic device to:

transmit second information including at least one of direction information of the ear with the tinnitus symptoms based on the first input, tinnitus frequency information based on the second input, or tinnitus state information based on the third input to an external server through the communication circuit;

receive a fourth sound source optimized for a tinnitus characteristic of the user, the fourth sound source being generated based on the received second information by the external server, from the external server through the communication circuit; and transmit a fourth control message configured to control a fourth sound source to be output through the external electronic device to the external electronic device through the communication circuit.

9. The electronic device of claim 1, wherein the instructions, when executed by at least one processor, individually and/or collectively, cause the electronic device to:

receive biometric information of a user, the biometric information being detected by the external electronic device while the user hears the at least one sound source via the external electronic device, from the external electronic device through the communication circuit, and wherein the first sound source includes a sound source in which a heart rate of the user is reduced while hearing the at least one sound source based on the received biometric information.

10. The electronic device of claim 1, further comprising:

a display, wherein the display is electrically connected with at least one processor, and wherein the instructions, when executed by at least one processor, individually and/or collectively, cause the electronic device to:

display specified guidance text on the display based on determining that the ambient noise has the specified level or more based on ambient noise information, and wherein the ambient noise information includes at least one of first ambient noise information detected by the electronic device or second ambient noise information detected by the external electronic device.

11. A method of operating an electronic device, the method comprising:

identifying an ear with tinnitus symptoms between a left ear and a right ear based on a first input selecting a direction of the ear with the tinnitus symptoms;

transmitting a first control message configured to control at least one test sound to be output through an external electronic device corresponding to the identified ear to the external electronic device;

determining a frequency corresponding to a selected test sound as a tinnitus frequency based on a second input selecting the one test sound among the at least one test sound output through the external electronic device;

generating a second sound source in which a portion corresponding to the tinnitus frequency is removed from a first sound source among at least one sound source;

transmitting a second control message configured to control the second sound source to be output through the external electronic device to the external electronic device; and based on determining that ambient noise has a specified level or more based on ambient noise information, controlling the external electronic device to remove at least part of the ambient noise during output of the at least one test sound through the external electronic device.

12. The method of claim 11, further comprising:

transmitting first information including at least one of direction information of the ear with the tinnitus symptoms based on the first input or tinnitus frequency information based on the second input to an external server;

receiving a third sound source optimized for a tinnitus characteristic of a user, the third sound source being generated based on the received first information by the external server, from the external server; and transmitting a third control message configured to control the third sound source to be output through the external electronic device to the external electronic device.

13. The method of claim 11, further comprising:

displaying a user interface including a question for evaluating a tinnitus state of a user on a display of the electronic device; and determining the tinnitus state of the user based on a third input selecting a response to the question.

14. The method of claim 13, further comprising:

displaying feedback information corresponding to the determined tinnitus state on the display.

15. The method of claim 14, wherein the feedback information includes at least one of whether tinnitus is alleviated, a tinnitus alleviation degree, whether tinnitus management is required, or a tinnitus alleviation method optimized for the determined tinnitus state.

16. The method of claim 14, further comprising:

transmitting tinnitus state information based on the third input to an external server; and receiving the feedback information from the external server, wherein the feedback information includes information received from a medical institution server as the external server shares the received tinnitus state information with the medical institution server.

17. The method of claim 16, wherein the feedback information includes at least one of tinnitus counseling information or tinnitus treatment information.

18. The method of claim 13, further comprising:

transmitting second information including at least one of direction information of the ear with the tinnitus symptoms based on the first input, tinnitus frequency information based on the second input, or tinnitus state information based on the third input to an external server;

receiving a fourth sound source optimized for a tinnitus characteristic of the user, the fourth sound source being generated based on the received second information by the external server from the external server; and transmitting a fourth control message configured to control the fourth sound source to be output through the external electronic device to the external electronic device.

19. The method of claim 11, further comprising:

receiving biometric information of a user, the biometric information being detected by the external electronic device while the user hears the at least one sound source via the external electronic device, from the external electronic device;

selecting a fifth sound source in which a heart rate of the user is reduced while hearing the at least one sound source based on the received biometric information; and transmitting a fifth control message configured to control the selected fifth sound source to be output through the external electronic device to the external electronic device.

20. The method of claim 11, further comprising:

displaying specified guidance text on a display of the electronic device based on determining that the ambient noise has the specified level or more based on ambient noise information, wherein the ambient noise information includes at least one of first ambient noise information detected by the external electronic device or second ambient noise information detected by the external electronic device.

* * * * *